(12) United States Patent
Koyama et al.

(10) Patent No.: US 6,407,112 B1
(45) Date of Patent: *Jun. 18, 2002

(54) OPTICALLY ACTIVE TETRAHYDROBENZINDOLE DERIVATIVE

(75) Inventors: Masao Koyama; Osamu Ushiroda; Chika Kikuchi; Takashi Ando; Eriko Morita; Masayo Okuno; Toyokazu Hiranuma, all of Kanagawa (JP)

(73) Assignee: Meiji Seika Kaisha, Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/673,833
(22) PCT Filed: Apr. 21, 1999
(86) PCT No.: PCT/JP99/02127
§ 371 (c)(1), (2), (4) Date: Oct. 23, 2000
(87) PCT Pub. No.: WO99/54303
PCT Pub. Date: Oct. 28, 1999

(30) Foreign Application Priority Data

Apr. 22, 1998 (JP) ............................................ 10-111833

(51) Int. Cl.[7] .................... C07D 209/92; C07D 401/06; C07D 471/04; A61K 31/435; A61K 31/44
(52) U.S. Cl. .................. 514/254.08; 544/373; 514/339; 514/307; 514/301; 514/292; 546/276.7; 546/148; 546/114; 546/85
(58) Field of Search ..................... 544/373; 514/254.08, 514/339, 307, 301, 292; 546/276.7, 148, 114, 85

(56) References Cited

FOREIGN PATENT DOCUMENTS

| WO | 98/00400 | 1/1998 | ......... C07D/209/92 |
|---|---|---|---|
| WO | WO 98/00400 | * 1/1998 | |

OTHER PUBLICATIONS

Kikuchi Yuka et al. Tetrahydrobenzindoles:selective of the 5–HT7 receptor, J. Med. Chem., 42:533–535, 1999.*
International Search Report.
Abstracts of Papers Part 1, 215th ACS National Meeting, 8412–3557–0, American Chemical Society, Dallas Texas, Mar. 29–Apr. 2, 1998.
U.S. application No. 09/582,416, filed Jun. 26, 2000, Kikuchi et al. pending.

* cited by examiner

Primary Examiner—Mukund J. Shah
Assistant Examiner—Hong Liu
(74) Attorney, Agent, or Firm—Sughrue Mion, PLLC

(57) ABSTRACT

Optically active tetrahydrobenzindole type compounds having affinity for a 5-HT receptor, useful for prevention and treatment of mental diseases. A species compound is (S)-2a-4-(4-(2-methoxyphenyl)piperazinyl)butyl)-2a,3,4,5,-tetrahydro 1 H-benz[cd]indol-2-one.

9 Claims, No Drawings

US 6,407,112 B1

OPTICALLY ACTIVE TETRAHYDROBENZINDOLE DERIVATIVE

TECHNICAL FIELD

The present invention relates to an optically active tetrahydrobenzindole derivative and a pharmaceutical composition containing the same. It also relates to an optically active intermediate suitable for producing the optically active compound, and a method for producing the optically active compound.

BACKGROUND ART

Since the function of serotonin (5-HT) in the central nervous system has been suggested, the classification and distribution of the serotonin receptor have been gradually clarified. According to a detailed analysis of the serotonin receptor using a recent molecular biological method, $5-HT_1$ and the subtype thereof, $5-HT_2$ and the subtype thereof, $5-HT_3$, $5-HT_4$, $5-HT_6$, $5-HT_7$ and the like have been specified, and fourteen kinds of serotonin receptors have been proposed (refer to R. D. Ward et al., Neuroscience, 64, 1105 to 1111, 1995).

Of these serotonin receptors, $5-HT_7$ abundantly present in a brain is considered to have an important function on the circadian rhythm regulation, both in human and animals (refer to T. W. Lovenberg et al., Neuron, 11, 449 to 458, 1993). It is also considered that $5-HT_7$ is present not only in a brain of human and animals, but also in a smooth muscle tissue, i.e., spleen, stomach, ileum, small intestine, coronary vessel or the like of human and animals (refer to A. J. Sleight, DN&P, 214 to 223, 1997), and performs various physiological functions. Accordingly, the creation of compounds acting on $5-HT_7$ receptor is extremely useful for the research of physiological functions in these organs, and also useful for treatment or prevention of diseases caused by an abnormality in a function in these organs.

The present inventors have already found a substance having a strong binding affinity for $5-HT_7$ receptor in an organism. Namely, according to the inventions by the present inventors (WO98/00400, and Japanese Patent Applications Nos. 9-358380, 9-358381 and 10-85913, corresponding to WO99/33804), there are provided a novel tetrahydrobenzindole derivatives which have strong affinity on cloned $5-HT_7$ receptor and a pharmaceutical composition characterized by containing the same.

By the above-described inventions, compounds which showed strong affinity on cloned $5-HT_7$ receptor could have been newly provided. However, details regarding an optically active compound present in the tetrahydrobenzindole derivative were still not clear. Now, it is widely known that an active substance to be bound with a receptor in an organism is one having a stereostructure desirably fitting in a compound binding site of the receptor. It is strongly desired to obtain a single optical isomer in view of clarification of physiological properties of a receptor and also the creation of a pharmaceutical composition. Accordingly, the object of the present invention is to obtain an optically active compound having a high selectivity on $5-HT_7$ receptor.

DISCLOSURE OF THE INVENTION

The present inventors have conducted investigations regarding tetrahydrobenzindole derivative from various points. Namely, regarding mutual separation of optically active compounds, conventionally, have been known methods, i.e., fractional crystallization and a utilization of a salt formation comprising an optically active acid and base. Recently, so-called chiral chromatography using an optically active carrier is known. However, in any method as described above, respective conditions of separation and fractionation of a compound must be selected. Further, these methods cannot necessarily be applied to all related compounds.

The present inventors could have solved the above-described problem by developing a novel synthesis route comprising an optical resolution in the stage of a raw material for synthesis and utilization of an optically active raw material. Specifically, according to the present invention, there are provided an optically active tetrahydrobenzindole derivative and a pharmaceutical composition containing the optically active compound, an optical intermediate suitable for producing the optically active compound, and a method for producing the optically active compound.

Accordingly, the present invention comprises the following construction.

1. An optically active compound represented by the following general formula (I):

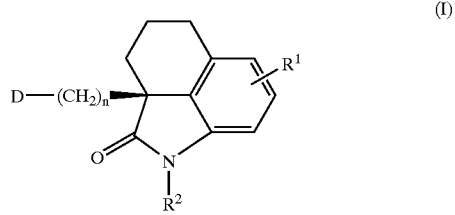

wherein D represents the following general formula (II), (IIIa), (IIIb), (IV), (V) or (VI):

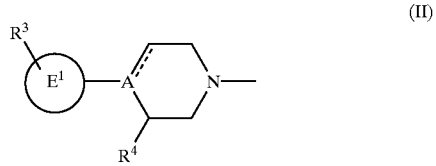

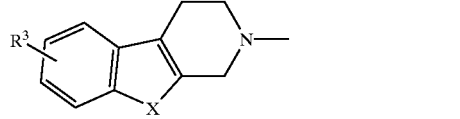

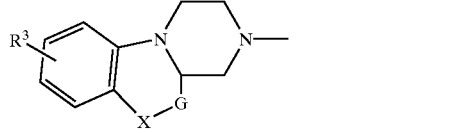

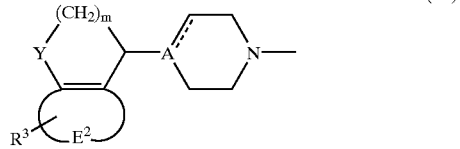

-continued (V)

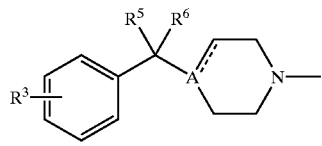

(VI)

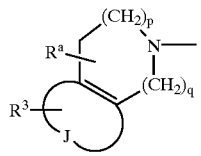

(VII)

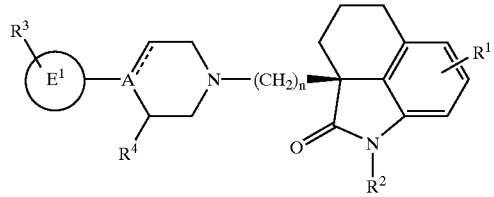

wherein $R^1$, $R^2$, $R^3$, $R^4$, A, $E^1$, and n have the same definitions as those of the item 1 above, and the pharmacologically acceptable salt thereof.

4. An optically active compound as described in item 3 above, wherein $E^1$ represents a group forming a pyridine ring or a pyrimidine ring; and A represents N, and the pharmacologically acceptable salt thereof.

5. An optically active compound as described in item 1 above represented by the following general formula (VIIIa):

(VIIIa)

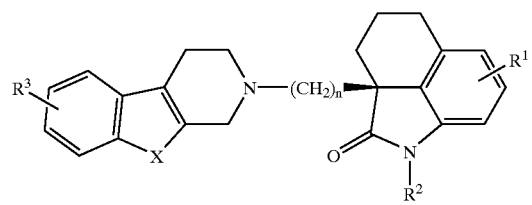

wherein $R^1$, $R^2$, $R^3$, X and n have the same definitions as those of the item 1 above, and the pharmacologically acceptable salt thereof 6. An optically active compound as described in item 1 above represented by the following general formula (VIIIb):

(VIIIb)

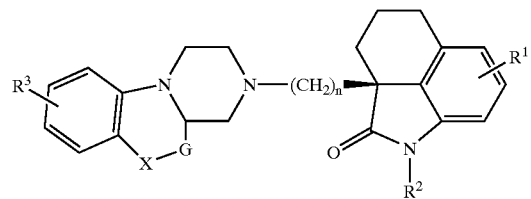

wherein $R^1$, $R^2$, $R^3$, X, G and n have the same definitions as those of the item 1 above, and the pharmacologically acceptable salt thereof.

7. An optically active compound as described in item 1 above represented by the following general formula (IX):

(IX)

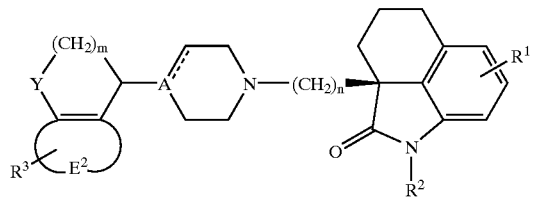

wherein $R^1$, $R^2$, $R^3$ A, $E^2$, Y, m and n have the same definitions as those of the item 1 above, and the pharmacologically acceptable salt thereof.

$R^1$ and $R^3$ each independently represents (single or plural) a hydrogen atom, a halogen atom, a lower alkyl, a cyano, a trihalomethyl, a hydroxy, an alkoxy, an alkylthio, an alkylsulfinyl, an alkylsulfonyl, a carboxy, an alkoxycarbonyl, an acyl, an acyloxy, an acylthio, a sulfamoyl, a nitro, an amino, an alkylamino, a carbamoyl, an alkylcarbamoyl or a phenyl;

$R^2$ and $R^4$ each independently represents a hydrogen atom, a lower alkyl or an aralkyl;

n represents an integer of 2 to 4;

A represents N, CH, C having a double bond or $CR^7$ ($R^7$ represents a lower alkyl, a cyano, a carbamoyl, an alkylcarbamoyl, a carboxy, an acyl, an acyloxy, an alkoxy, an alkoxycarbonyl, trihalomethyl or a hydroxy;

=== represents a single bond or a double bond;

G represents a methylene or a carbonyl;

$E^1$ represents a group forming a benzene ring, a pyridine ring or a pyrimidine ring;

$E^2$ represents a group forming a benzene ring, a pyridine ring or a pyrimidine ring together with a carbon atom having a double bond in a condensed part;

J represents a group forming a benzene ring, a thiophene ring, a furan ring, an imidazole ring or a pyrazole ring together with a carbon atom having a double bond in a condensed part;

X represents $NR^8$, $NCONR^9R^{10}$, S, SO, $SO_2$ or O (in which $R^8$ represents a hydrogen atom, a lower alkyl, an aralkyl, an oxoalkyl, an alkenyl, a cyanoalkyl, a hydroxyalkyl, an alkoxyalkyl, an aminoalkyl, an alkylaminoalkyl, an alkoxycarbonylalkyl, a carbamoylalkyl, an alkylcarbamoylalkyl, an acyl or an alkoxycarbonyl, $R^9$ and $R^{10}$ each independently represents a hydrogen atom or a lower alkyl);

Y represents $CH_2$, S, O or CO;

$R^5$ and $R^6$ each independently represents a hydrogen atom, a lower alkyl, a hydroxy, an alkoxy, an acyl or a phenyl;

$R^a$ represents a hydrogen atom or an alkyl;

m represents an integer of 1 to 3;

p represents an integer of 0 or 1 to 3;

q represents an integer of 0 or 1 to 3, provided that p+q represents an integer of 1 to 3;

and the pharmacologically acceptable salt thereof.

2. An optically active compound as described in item 1 above, wherein n is 4, and the pharmacologically acceptable salt thereof.

3. An optically active compound as described in item 1 or 2 above represented by the following general formula (VII):

8. An optically active compound as described in item 7 above, wherein $E^2$ represents a group forming a pyridine ring or a pyrimidine ring together with a double bond; and A represents N, and the pharmacologically acceptable salt thereof.

9. An optically active compound as described in item 1 above represented by the following general formula (X):

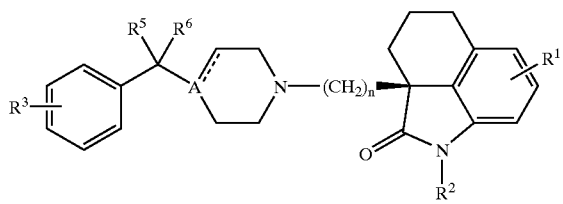

(X)

wherein $R^1$, $R^2$, $R^3$, $R^5$, $R^6$, A and n have the same definitions as those of the item 1 above, and the pharmacologically acceptable salt thereof.

10. An optically active compound as described in item 1 above represented by the following general formula (XI):

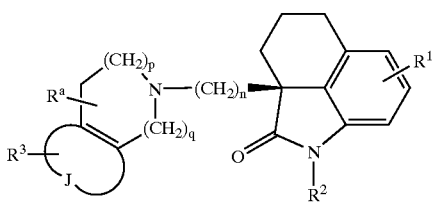

(XI)

wherein $R^1$, $R^2$, $R^3R^a$, J, n, p, q and p+q have the same definitions as those of the item 1 above, and the pharmacologically acceptable salt thereof.

11. A pharmaceutical composition characterized by comprising an optically active compound described in anyone of items 1 to 10 above or the pharmacologically acceptable salt thereof.

12. A pharmaceutical composition for the treatment or prevention of mental diseases characterized by comprising an optically active compound described in anyone of items 1 to 10 above or the pharmacologically acceptable salt thereof.

13. 5-$HT_7$ agent characterized by comprising an optically active compound described in anyone of items 1 to 10 or the pharmacologically acceptable salt thereof.

14. An optically active compound represented by the following general formula (XII):

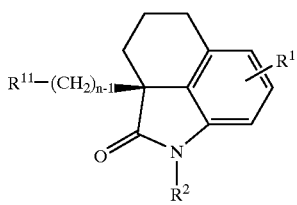

(XII)

wherein $R^1$, $R^2$ and n have the same definitions as those of the item 1 above; $R^{11}$ represents an aldehyde, an alkoxycarbonyl, a carboxyl and the salt thereof, or $CH_2Z$ (Z represents a hydroxy or a leaving group).

EMBODIMENTS OF THE INVENTION

In the present specification 5-$HT_7$ agent means a substance having a strong binding affinity to a 5-$HT_7$ receptor in an organism.

In the description regarding the chemical substances and the production thereof in the present specification, for example, a halogen atom means fluorine, chlorine, bromine or iodine atom, a lower alkyl means a straight chain alkyl having 1 to 4 carbon atoms typically represented by a methyl group, an ethyl group, and the like; and a branched chain alkyl such as iospropyl, isobutyl and t-butyl. A base to be used as a catalyst means an inorganic base such as sodium hydroxide and potassium carbonate, an organic base such as triethylamine, pyridine and dimethylaniline. A substituent means a group other than a hydrogen atom.

Definition of Substituent

In the general formulae (I) to (XIII), substituents, $R^1$ and $R^3$ each independently represents (single or plural) a halogen atom, a lower alkyl, a cyano, a trihalomethyl (the halogen atoms have the same definition as described above, three halogen atoms may be the same or different, preferably trifluoromethyl), a hydroxy, an alkoxy (preferably having 1 to 4 carbon atoms, e.g., methoxy, ethoxy and the like), an alkylthio (preferably having 1 to 4 carbon atoms, e.g., methylthio, ethylthio and the like), alkylsulfinyl (preferably having 1 to 4 carbon atoms, methanesulfinyl), an alkylsulfonyl (preferably having 1 to 4 carbon atoms), a carboxy, an alkoxycarbonyl (preferably having 1 to 4 carbon atoms), an acyl (preferably having 1 to 4 carbon atoms, e.g., acetyl), an acyloxy (preferably alkyl moiety has 1 to 4 carbon atoms, e.g., acetoxy), an acylthio (preferably having 1 to 4 carbon atoms, e.g., acetylthio), a sulfamoyl, a nitro, an amino, an alkylamino (in the specification of the present application, an alkylamino means one wherein a nitrogen atom has at least one alkyl substituent, preferably an amino substituted with a lower alkyl, e.g., methylamino, ethylamino, dimethylamino, diethylamino), a carbamoyl, an alkylcarbamoyl (in the specification of the present application, an alkylcarbamoyl means one wherein a nitrogen atom has at least one alkyl substituent, preferably one wherein an alkyl moiety is a lower alkyl, e.g., methylcarbamoyl, dimethylcarbamoyl, and the like) or a phenyl.

Substituents, $R^2$ and $R^4$ each represents preferably a lower alkyl or an aralkyl (preferably benzyl, substituted benzyl).

n represents an integer of 2 to 4, preferably 4.

Substituents $R^5$ and $R^6$ each independently represents a lower alkyl (preferably, having 1 to 4 carbon atoms), a hydroxy, an alkoxy (preferably having 1 to 4 carbon atoms, e.g., methoxy, ethoxy and the like), an acyl or a phenyl.

Substituent, $R^a$ represents an alkyl (preferably, having 1 to 4 carbon atoms)

A represents N, CH, C having a double bond or $CR^7$ (in formulae (II), (IV) and (V), the dotted line from A means a chemical bond in the case where A is C having a double bond, $R^7$ represents a lower alkyl (preferably having 1 to 4 carbon atoms), a cyano, a carbamoyl, an alkylcarbamoyl (preferably methylcarbamoyl, diethylcarbamoyl, and the like), a carboxy, an acyl (preferably acetyl, propionyl, and the like), an acyloxy (preferably methoxy, ethoxy, and the like), an alkoxycarbonyl (preferably methoxycarbonyl, ethoxycarbonyl, and the like), a trihalomethyl (preferably trifluoromethyl and the like) or a hydroxy.

G represents a methylene or a carbonyl.

In general formula (II), $E^1$ represents a group forming a benzene ring, a pyridine ring or a pyrimidine ring for itself, in general formula (IV), $E^2$ represents a group forming a benzene ring, a pyridine ring or a pyrimidine ring together with a carbon atom having a double bond in a condensed part.

In a case where $E^1$ and $E^2$ form a pyridine ring or a pyrimidine ring, A is preferably N.

J represents a group forming a benzene ring, a thiophene ring, a furan ring, an imidazole ring or a pyrazole ring, preferably a benzene ring or a thiophene ring, together with a carbon atom having a double bond in a condensed part.

X is a substituted or non-substituted hetero atom in a hetero aromatic ring consisting of condensed three rings. In general formula (IIIa), when X is an oxygen atom, it forms a benzofuran ring together with an adjacent benzene ring; when X is a sulfur atom, it forms a benzothiophene ring together with an adjacent benzene ring; and when X is a nitrogen atom, it forms an indole ring together with an adjacent benzene ring. Similarly, in general formula (IIIb), X forms a condensed ring with a six-membered ring containing a nitrogen atom corresponding to the same formula together with an adjacent benzene ring. When X is a sulfur atom, it may be substituted with oxygen. While, when it is a nitrogen atom, it may be substituted with a substituent other than a hydrogen atom, such as a substituent, $R^8$ or $CONR^9R^{10}$.

Substituent $R^8$ herein represents a lower alkyl (preferably having 1 to 4 carbon atoms), an aralkyl (preferably benzyl or substituted benzyl), an oxoalkyl (preferably oxopropyl), an alkenyl (preferably allyl), a cyanoalkyl (preferably cyanomethyl, cyanoethyl), a hydroxyalkyl (preferably hydroxymethyl and hydroxyethyl), an alkoxyalkyl (preferably methoxymethyl, methoxyethyl, ethoxymethyl and ethoxyethyl), an aminoalkyl (preferably aminoethyl, methylaminoethyl and dimethylaminoethyl), an alkylaminoalkyl, an alkoxycarbonylalkyl (preferably methoxycarbonylmethyl, ethoxycarbonylmethyl, methoxycarbonylethyl and ethoxycarbonylethyl), a carbamoylalkyl (preferably carbamoylmethyl), an alkylcarbamoylalkyl (in the specification of the present application, an alkylcarbamoylalkyl means one wherein a nitrogen atom has at least one of alkyl substituent, preferably methylcarbamoylmethyl and dimethylcarbamoylmethyl), an acyl (preferably acetyl and propionyl) or an alkoxycarbonyl (preferably methoxycarbonyl, ethoxycarbonyl and benzyloxycarbonyl); substituents, $R^9$ and $R^{10}$ each independently represents a lower alkyl (preferably having 1 to 4 carbon atoms).

Y represents $CH_2$, S, O or CO; m represents an integer of 1 to 3, preferably 2; examples of a substituent for A in general formula (IV) are those forming 1-indanyl, 1,2,3,4-tetrahydronaphthalene-1-yl, 6,7,8,9-tetrahydro-5H-benzocycloheptene-5-yl, 9-oxo-6,7,8,9-tetrahydro-5H-benzocycloheptene-5-yl, 4-chromanyl, 4-thiochromanyl, and the like.

p represents an integer of 0 or 1 to 3, preferably 1 or 2; q represents an integer of 0 or 1 to 3, preferably 0 or 1, provided that p+q represents an integer of 1 to 3, preferably 2. Namely, in the general formula (VI), a secondary amino group bonded with a methylene chain forms a 5 to 7-membered ring, preferably a 6-membered ring. This substituent is condensed with group J forming a benzene ring, a thiophene ring, a furan ring, an imidazole ring or a pyrazole ring so that formula (VI) represents an indolinyl, a tetrahydroquinolyl, a tetrahydroisoquinolyl, a 2,3,4,5-tetrahydro-1H-benzo[b]azepinyl, a 2,3,4,5-tetrahydro-1H-benzo[c]azepinyl, a 2,3,4,5-tetrahydro-1H-benzo[d]azepinyl, a 4,5,6,7-tetrahydrothieno[3,2-c]pyridyl, a 4,5,6,7-tetrahydrofuro[3,2-c]pyridyl, a 4,5,6,7-tetrahydropyrazolo[4,3-c]pyridyl, and the like.

In general formula (XII), $R^{11}$ represents an aldehyde, an alkoxycarbonyl, a carboxyl and the salt thereof, or $CH_2Z$ (Z represents a hydroxy or a leaving group).

Here, as the leaving group, for example, mention may be made of a halogen atom (e.g., chlorine atom, bromine atom, iodine atom), an alkylsulfonate residue (methanesulfonyloxy, ethanesulfonyloxy and the like), and an arylsulfonate residue (benzenesulfonyloxy, p-toluenesulfonyloxy and the like).

$R^1$ and $R^3$ in general formulae (I) to (XII) or $R^a$ in general formula (VI) is a symbol which can represent all hydrogen atoms present in the ring. In a case where $R^1$, $R^3$ or $R^a$ is a substituent, they can be independently substituted with any hydrogen atom present in the ring. It is possible that they are not substituted or partially substituted (one position or plural positions). In the latter case, the substituents may be the same or different.

In the present invention, in an optically active compound represented by the general formula (I) (hereinafter, also referred to as "compound (I)", in the other formula, the compound is also called similarly) and a compound (XII), an absolute configuration of an asymmetric carbon in the position 2a in a tetrahydrobenzindole skeleton is S configuration.

An optically active compound provided by the present invention is produced according to the chemical synthesis method set forth below.

Synthesis Method of Compound (I)

First, the compound (I) can be obtained by reacting a compound (XIII), which is a reactive optically active intermediate of the present invention, with an amine represented by D–H as shown by the following reaction formula:

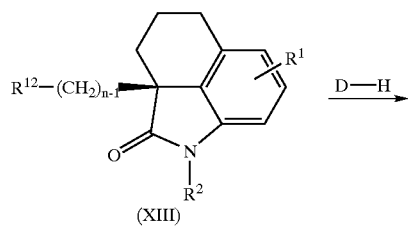

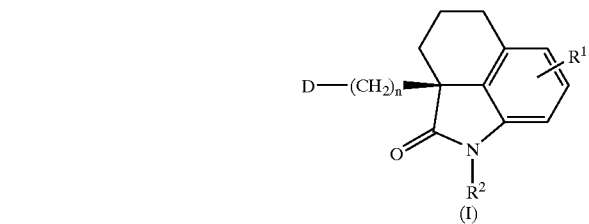

wherein $R^1$, $R^3$, n and D have the same definitions as those described above; $R^{12}$ represents an aldehyde or $CH_2W$ (W is a leaving group).

When $R^{12}$ is $CH_2W$, the reaction for obtaining the compound (I) is conducted in the absence of a solvent or conducted after diluted with an inert solvent, in the presence or absence of a base at atmospheric temperature to an elevated temperature. Examples of the inert solvent used include dioxane, tetrahydrofuran, acetonitrile and dimethylformamide. Examples of the base include alkali carbonates (e.g., sodium carbonate, potassium carbonate and the like), alkali bicarbonates (sodium bicarbonate, potassium bicarbonate and the like), trialkylamines and pyridine bases.

Further, a secondary amine itself used as a starting material can be excessively used. As the leaving group W, those as described in the above-described Z can be mentioned.

When $R^{12}$ represents an aldehyde, a desired optically active compound of the compound (I) can be obtained by reductive aminoalkylation using sodium triacetoxyborohydride.

Synthesis of Compound (XII) or Compound (XIII) (Optically Active Intermediate)

Next, the compound (XII) or the compound (XIII), i.e., an optically active intermediate, which is another stating material to be used in the synthesis of an optically active compound represented by the general formula (I) in the present invention (hereinafter, also referred to as an "intermediate of the present invention") can be produced using a commercially available reagent according to the following process.

Namely, 2a, 3, 4, 5-tetrahydro-1H-benz[cd]indol-2-one (XIV) as the starting material is reacted with a compound (XV) in the presence of a base to form a compound (XVI).

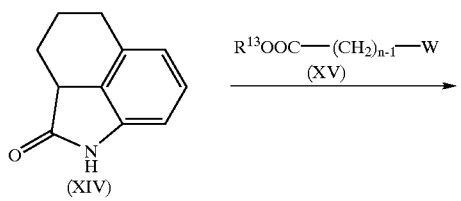

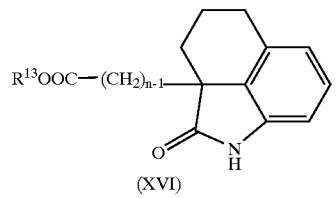

wherein W represents a leaving group, n represents an integer of 2 to 4, $R^{13}$ represents a lower alkyl group.

As the compound (XV) shown in the above-described reaction formula, for example, mention may be made of those wherein W represents a halogen atom (e.g., chlorine atom, bromine atom, iodine atom), an alkylsulfonate residue (methanesulfonyloxy, ethanesulfonyloxy or the like), an arylsulfonate residue (benzenesulfonyloxy, p-toluenesulfonyloxy or the like), preferably chloroacetates, bromoacetates, 3-bromopropionates and 4-bromobutyrates.

These compounds can be available as synthetic reagents or can be obtained by the synthesis according to a halogenation of a hydroxylate represented by the formula: HO—$(CH_2)_{n-1}$—$COOR^{13}$ (in the formula, n and $R^{13}$ represent those as described above)

Examples of the halogenating agent include thionyl chloride and thionyl bromide. Other examples of the halogenation include the use of carbon tetrachloride or carbon tetrabromide in the presence of triphenylphosphine.

While as W, if a sulfonate residue such as an alkylsulfonyloxy residue and an arylsulfonyloxy residue is introduced instead of a halogen atom, the resulting compound also can be used as the starting material. Namely, an alkylsulfonyl halide such as methanesulfonyl chloride or an arysulfonyl halide such as benzenesulfonyl chloride can be reacted to obtain the compound (XV) as a sulfonate.

Next, a compound (XVI) is converted to a carboxylic acid shown by the formula (XVII) by the hydrolysis as shown in the following reaction formula.

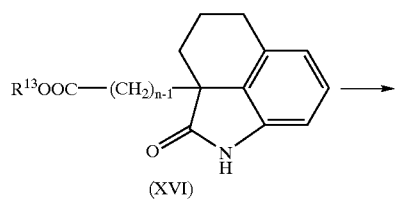

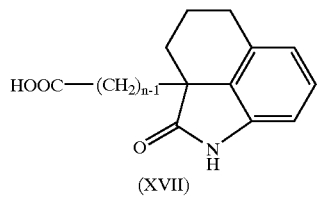

wherein n and $R^{13}$ are the same as those described above.

The hydrolysis can be carried out usually in the presence of an alkali, for example, sodium hydroxide, in water, an organic solvent miscible with water at any proportion (for example, alcohols such as methanol, ethers such as ethylene glycol dimethylether, dioxane and tetrahydrofuran), or a mixture of such an organic solvent with water.

A compound (XVII) is further fractionated to an optically active compound (XVIII) by forming a salt with an optically active base, as shown in the following formula:

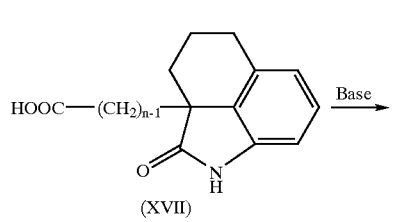

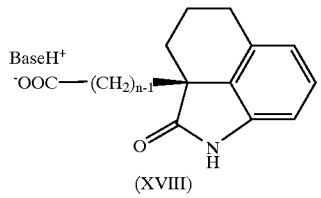

wherein n is the same as described above.

In this formula, Base is the general term for an optically active organic base. A chiral amine (preferably optically active phenethylamine and the like), a chiral aminoalcohol (preferably an optically active valinol and the like) are used in the present process. Other well-known natural chemical substances such as cinchonine and cinchonidine agree with the object of the separation of an optically active compound.

The optically active carboxylic acid separated as a salt is converted to a free acid, then used in the successive process as shown in the following reaction formula. Specifically, the free acid (XIX) is esterified again to obtain a compound (XX), which is successively reduced to an alcohol (XXI). Further, the hydroxyl group is converted to a reactive halogen or another substituent to form an optically active intermediate (XXII). Alternatively, the free acid is directly reduced to form an aldehyde (XXIII) or the alcohol (XXI). The aldehyde (XXIII) also can be produced by the oxidation of the alcohol (XXI).

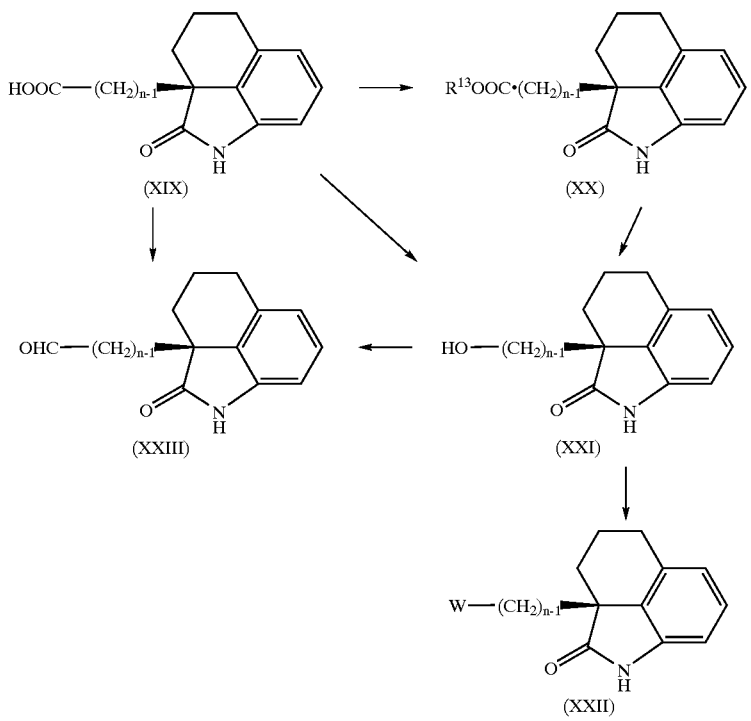

wherein $R^{13}$, n and W represent those as described above.

Specifically, the re-esterification comprises, for example, a conversion to a methylester with an alcohol, e.g., methanol, in the presence of an acidic catalyst such as hydrochloric acid or sulfuric acid. The synthesis from the ester (XX) thus obtained to the alcohol (XXI) can be carried out using a well-known reducing agent, e.g., lithium borohydride or borane. The alcohol (XXI) thus obtained is converted to the reactive compound (XXII) by converting the hydroxyl group to a halogen derivative or a sulfonate. The direct reduction of the carboxylic acid or the oxidation of the alcohol (XXI), for example, oxidation by manganese dioxide or another oxidizing agent, provides the aldehyde compound (XXIII), which is also a useful substance. It should be additionally mentioned that the aldehyde compound (XXIII) exhibits the similar effects to those of the compound (XXII) activated in the process of the present invention.

The optically active intermediate compound provided by the present invention has a quarternary carbon atom in the optically active center and maintains the optical activity during these processes. In other word, the optically active intermediate compound has such a characteristic that the decrease in the optical purity thereof by racemization is extremely small.

If desired, a substituent can be introduced into the tetrahydrobenzindole ring during which the optical activity is maintained.

Specifically, as shown in the following reaction formula, the introduction of an optional substituent to the benzene ring and/or the introduction of a substituent to the amide nitrogen can be carried out without deteriorating the optical purity of the intermediate compound.

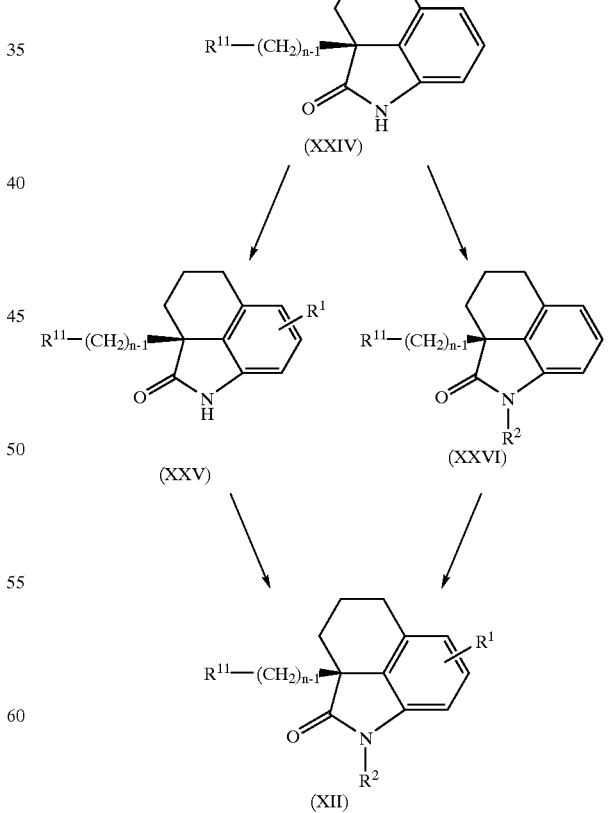

wherein $R^1$, $R^2$, $R^{11}$ and n represent those as described above.

The details regarding the introduction of these substituents in the racemic compounds are disclosed in WO98/00400 by the present inventors.

Various kinds of optically active intermediates of the present invention (XII) thus obtained constitute a group of useful compounds as the starting materials of medicines. Specifically, they are extremely useful for the production of an optically active compound having the following formula (I) provided according to the present invention.

The significance of the intermediate of the present invention (XII) is now clarified. However, in particular, the reactive intermediate of the present invention (XIII) can be further widely applicable to various products. Namely, it is specially mentioned that the intermediate is a suitable substance for the production of another pharmaceutical composition, particularly, physiologically active amines.

An Amines D–H

The details of an amine D to H which is another starting material used in the synthesis of the optically active compound shown by the general formula (I) in the present invention are as follows. Regarding the details of the synthesis of the amine, WO98/00400 or PCT/JP98/05827 can be referred to.

First, regarding the case where D is an amine represented by the general formula (II), examples of such an amine include 1-phenylpiperazines, 4-phenylpiperidines, 4-phenyl-1,2,3,6-tetrahydropyridines, 1-(2-pyridyl)piperazines, and 1-(2-pyrimidinyl)piperazines.

Next, in a case where D is an amine represented by the general formula (IIIa), a synthesis method of such an amine will be described in detail below.

In the general formula (IIIa), when X represents either $NR^8$ or $NCOR^9R^{10}$, an amine can be obtained by using commercially available 2,3,4,9-tetrahydro-1H-pyrido[3,4-b]indoles or can be derived from a commercially available tryptamine derivative and formaldehyde through Pictet-Spengler reaction (for example, Organic Reactions, 6, 151, 1951). Alternatively, also can be used 2,3,4,9-tetrahydro-1H-pyrido[3,4-b]indole derived from these compounds through various chemical reactions wherein 9-position is modified. Examples of such 9-position modified compound include a 9-alkyl derivative, a 9-alkenyl derivative, a 9-acyl derivative, a 9-carbamoyl derivative, and a 9-alkoxycarbonyl derivative.

The above-described 9-position modification product of 2,3,4,9-tetrahydro-1H-pyrido[3,4-b]indole can be obtained by protecting the secondary amino group present in 2-position of 2,3,4,9-tetrahydro-1H-pyrido[3,4-b]indole with an ordinary used protecting group, then effecting a chemical reaction such as alkylation or acylation, followed by deprotecting the protecting group. It is preferable that the protecting group to be used is stable under the conditions of the chemical reaction such as alkylation or acylation, and is readily subjected to the deprotection. Examples of the protecting group include carbamates such as a t-butoxycarbonyl group and a benzyloxycarbonyl group.

For example, the synthesis of the above-described 9-position modification product of 2,3,4,9-tetrahydro-1H-pyrido[3,4-b]indole is preferably conducted by diluting the 2,3,4,9-tetrahydro-1H-pyrido[3,4-b]indole derivative wherein the secondary amino group present in 2-position thereof is protected, with an inert solvent such as tetrahydrofuran, diethyl ether, toluene, 1,2-dimethoxyethane, dimethylformamide or dimethylsulfoxide in the presence of a strong base such as sodium hydride, n-butyl lithium or lithium diisopropylamide at a low temperature to an elevated temperature. Examples of the alkylating agent to be used include straight chain alkyl halides such as methyl iodide and ethyl bromide, branched chain alkyl halides such as isopropyl bromide and isobutyl bromide, chloromethyl methylether, bromoacetonitrile, benzyl bromide, bromoacetoamide, bromomethylacetate, and 2-chloro-N,N-dimethylethylamine. Examples of the acylating agent to be used include acyl halides such as acetyl chloride, propionyl chloride and isobutyryl chloride, dimethylcarbamoyl chloride, diethylcarbamoyl chloride, chloromethyl formate, and chloroethyl formate.

The 9-carbamoyl derivative or the 9-alkoxycarbonyl derivative of 2,3,4,9-tetrahydro-1H-pyrido[3,4-b]indole can be synthesized by chloroformylating 2,3,4,9-tetrahydro-1H-pyrido[3,4-b]indole with triphosgene in an inert solvent such as tetrahydrofuran, diethyl ether, toluene, 1,2-dimethoxyethane, dimethylformamide or dimethylsulfoxide in the presence of a strong base such as sodium hydride, n-butyl lithium or lithium diisopropylamide, then reacting the chloroformylated product with an amine such as ammonia or methylamine, or with an alcohol such as methanol or ethanol.

In the general formula (IIIa), in the case where X represents S, SO, $SO_2$ or O, an amine can be synthesized according to a conventionally known method. For example, 3,4-dihydro-1H-benzo[4,5]thieno[2,3-c]pyridine can be synthesized by cyclization of ethyl 4-(phenylthio)acetoacetate obtained from substituted or non-substituted thiophenol and ethyl 4-chloroacetoacetate, then amidation of the resulting cyclized product, reduction of the resulting amide, and Pictet-Spengler cyclization of the resulting product (J. Heterocylic Chem., 16, 1321, 1979). Further, by oxidizing the sulfur atom in the 9-position of the compound (IIIa), it can be converted to a sufoxide derivative or a sulfone derivative. For example, the amino group in 2-position of 3,4-dihydro-1H-benzo[4,5]thieno[2,3-c]pyridine is protected with a protecting group such as a t-butoxycarbonyl group or a benzyloxycarbonyl group, thereafter, the sulfur atom is selectively oxidized with m-chloroperbenzoic acid or hydrogen peroxide, followed by deprotecting the protecting group. Thus, 3,4-dihydro-9-oxo-9-$\lambda^4$-1H-benzo[4,5]thieno[2,3-c]pyridine or 3,4-dihydro-9,9-dioxo-9-$\lambda^6$-1H-benzo[4,5]thieno[2,3-c]pyridine can be obtained. While, 3,4-dihydro-1H-benzo[4,5]furo[2,3-c]pyridine can be synthesized, for example, by reduction of 3-cyanomethylbenzo[b]furan obtained from 3-(2H)-benzo[b]furanone and diethylcyanomethyl phosphate, formamidation of the resulting reduced product, cyclization of the formamidated product, and the reduction of the resulting imine (JP-A-63-22581) (The term "JP-A" as used herein means an "unexamined published Japanese patent application").

An amine represented by the general formula (IIIb) will be described below.

In the case where X represents O, and G represents methylene, an amine can be synthesized according to the conventionally known method. Specifically, as shown in the following reaction formula, the primary amino group of a benzoxazine derivative (IIIb-1) (Gupta. S. P. et al., Synthesis, 9, 660, 1974) is protected with an appropriate protecting group (Q) such as a benzoxycarbonyl group to obtain a compound (IIIb-2). The resulting compound (IIIb-2) is converted to a chloroacetylated derivative (IIIb-3) and then cyclized to a pyrazinobenzoxazine derivative (IIIb-4). The compound obtained is then converted to a compound (IIIb-5) by the reduction of the amide, successively the protecting group (Q) is removed therefrom to form an amine compound (IIIb-6) having the general formula (IIIb) (E. W. Baxter et al., Bioorg Med. Chem. Lett. 7,763, 1997).

In the case where X represents S, SO, $SO_2$ or O, and G represents methylene, 1,2,3,4,4a,5-hexahydropyrazino[2,1-c]-1,4-benzthiazine can be synthesized from a conventionally known compound, 3,4-dihydro-3-aminomethyl-2H-1,4-benzthiazine (P. Melloni et al., J. Heterocyclic Chem., 20, 139, 1983) according to the following method. Namely, the sulfur atom present in 6-position of a compound (IIIb-5) is selectively oxidized with m-chlorobenzoic acid or hydrogen peroxide, followed by deprotecting the protecting group, whereby an amine compound of a sulfoxide derivative and a sulfone derivative having the general formula (IIIb) can be obtained.

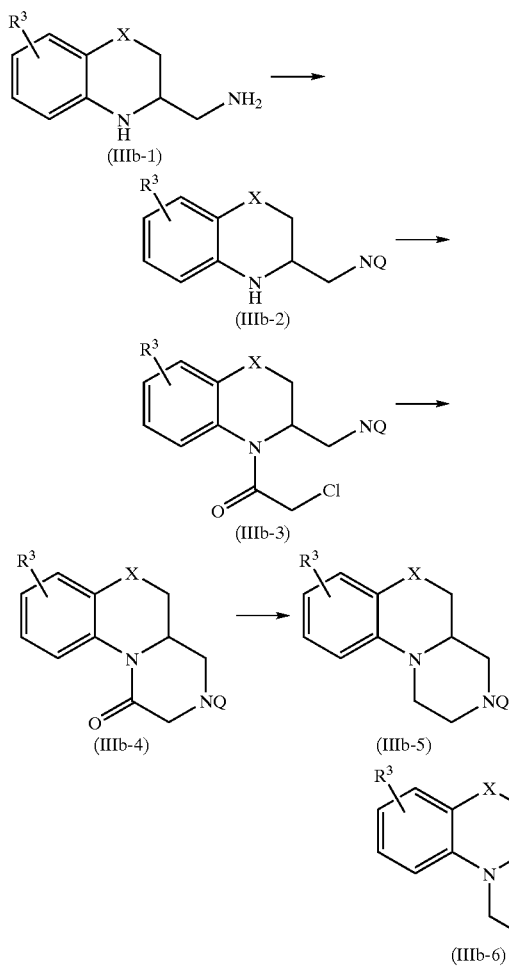

In the case where X represents $NR^8$ or $NCONR^9R^{10}$, and G represents carbonyl or methylene, a compound having the general formula (IIIb) can be synthesized by effecting a chemical modification such as alkylation or acylation of a conventionally known compound, 2,3,4,4a-tetrahydro-1H-pyrazino[1,2-a]quinoxaline-5(6H) -one derivative or 2,3,4, 4a,5,6-hexahydro-1H-pyrazino[1,2-a]quinoxaline derivative (JP-A-52-114000). For example, 2,3,4,4a-dihydro-tetrahydro-1H-pyrazino[1,2-a]quinoxaline-5(6H)-one wherein 3-position thereof is protected with an appropriate protecting group such a benzyloxycarbonyl group is reacted with an alkylating agent such as methyl iodide or ethyl bromide in the presence of a base such as sodium hydride so that an alkyl group may be introduced to the amide nitrogen. 2,3,4,4a,5,6-hexahydro-1H-pyrazino[1,2-a]quinoxaline wherein 3-position thereof is protected with an appropriate protecting group such a benzyloxycarbonyl group is reacted with an acylating agent such as an acyl halide (e.g., acetyl chloride, propionyl chloride, isobutyryl chloride), anhydrous trifluoroacetate, dimethylcarbamoyl chloride, diethylcarbamoyl chloride, chloromethyl formate, or chloroethyl formate in the presence of a base such as triethylamine, whereby a compound having the general formula (IIIb), the 6-position modification product, can be obtained.

Next, a synthesis method of an amine wherein D is represented by the general formula (IV) will be described in detail below.

An amine (IV-6) wherein D is represented by the general formula (IV) is synthesized as follows: The corresponding ketone having the formula (IV-1) ($R^3$, $E^2$, Y and m are the same as described above) is reduced with sodiumborohydride to an alcohol having the formula (IV-2), the alcohol (IV-2) obtained is chlorinated using thionyl chloride to form a compound (IV-3), successively, the compound (IV-3) obtained is condensed with N-t-butoxycarbonyl piperazine represented by the formula (IV-4) in the presence of a base to obtain a compound (IV-5), then, the resulting compound (IV-5) is subjected to de-t-butoxycarbonylation under an acidic condition.

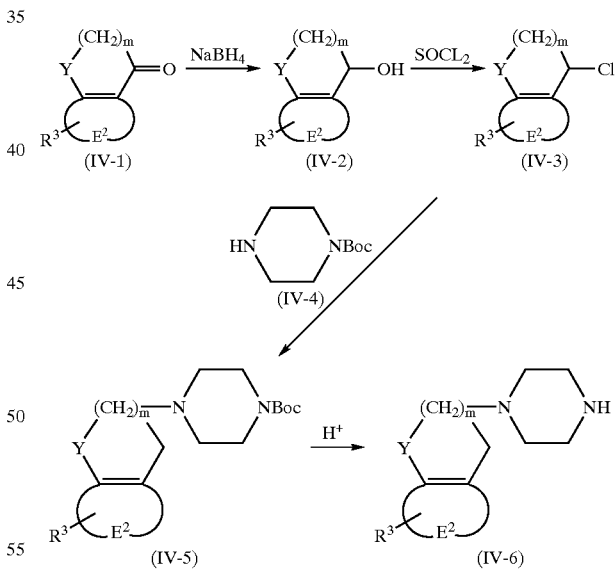

Alternatively, an amine (IV-9) wherein D is also represented by the formula (IV) is synthesized by reacting 4-bromopyridine shown by the formula (IV-7) with the corresponding ketone shown by the formula (IV-1) using n-butyl lithium in an ether to form a compound (IV-8), successively reducing the resulting compound (IV-8) in hydrogen atmosphere using platinum oxide as a catalyst.

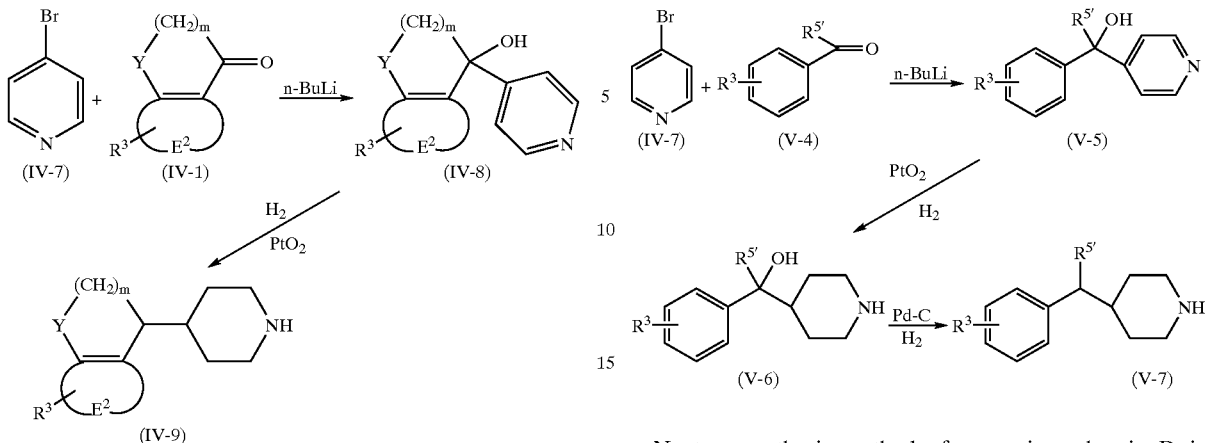

Next, a synthesis method of an amine wherein D is represented by the general formula (V) will be described in detail below.

An amine (V-3) wherein D is represented by the general formula (V) is synthesized by condensing a compound (V-1) (in the formula, Hal represents a halogen atom; $R^5$ and $R^6$ have the same definitions as those described above) with N-t-butoxycarbonyl piperazine represented by the formula (IV-4) in the presence of a base to obtain a compound (V-2), then, effecting de-t-butoxycarbonylation of the resulting compound (V-2) in an acidic condition.

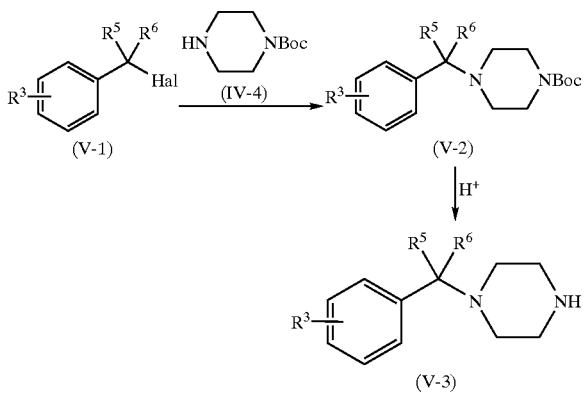

Alternatively, an amine (V-6) and (V-7) wherein D is represented by the general formula (V) is synthesized by reacting 4-bromopyridine shown by the formula (IV-7) with a corresponding ketone shown by the formula (V-4) (in the formula $R^3$ is the same as described above, $R^{5'}$ represents a lower alkyl or a phenyl) using n-butyl lithium in an ether to form a compound (V-5), successive reduction of the resulting compound (V-5) in hydrogen atmosphere using platinum oxide as a catalyst (V-6), then further reduction of the resulting product using palladium carbon as a catalyst (V-7).

Next, a synthesis method of an amine wherein D is represented by the general formula (VI) (hereinafter, also referred to as a compound (VI)) will be described in detail below.

In the case where J forms a benzene ring together with the carbon atom having a double bond in the condensed part, and p+q=3, the compound (VI) can be derived from a conventionally known compound, 2,3,4,5-tetrahydro-benzo[c]azepine-1-one or 1,3,4,5-tetrahydro-benzo[b]azepine-2-one (Tetrahedron, 49, 1807, 1993).

Of the compound (VI), in the case where J forms a thiophene ring together with the carbon atom having a double bond in the condensed part, various derivatives of the compound (VI) can be derived from conventionally known compounds, 4,5,6,7-tetrahydrothieno[3,2-c]pyridine-2-carboxylic acid (JP-A-5-60836), 4,5,6,7-tetrahydrothieno[2,3-c]pyridine-2-carboxylic acid, 5,6,7,8-tetrahydro-4H-thieno[3,2-c]azepine-2-carboxylic acid, or 5,6,7,8-tetrahydro-4H-thieno[2,3-c]azepine-2-carboxylic acid (WO94/21599).

While, of the compound (VI), in the case where J forms a furan ring together with the carbon atom having a double bond in the condensed part, various derivatives of the compound (VI) can be synthesized from conventionally known compounds, 4,5,6,7-tetrahydrofuro[3,2-c]pyridine, 4,5,6,7-tetrahydrofuro[2,3-c]pyridine, 5,6,7,8-tetrahydro-4H-furo[2,3-c]azepine, or 5,6,7,8-tetrahydro-4H-furo[2,3-d]azepine (JP-A-9-118681).

In the case where J forms a pyrazole ring together with the carbon atom having a double bond in the condensed part and p is 0, the compound (VI) can be synthesized according to a conventionally known method (JP-A-6-73056).

Salts and Pharmaceutical Composition

An optically active compound of the general formula (I) provided according to the present invention is an amine, which is present as a base. Therefore, the optically active compound of the general formula (I) forms salts with many kinds of inorganic acids and organic acids. This property is utilized in the production of a pure substance and also utilized when the compound is provided as a pharmaceutical composition. Specifically, in the production of a pure substance, the compound can be solubilized in a polar solvent such as water by acidifying the same, then extracted and purified, and isolated as the form of a salt showing desirable physical-chemical properties. While in the use as a pharmaceutical composition, the compound can have a form of a pharmacologically acceptable salt. As the possible form of the salt, mention may be made of acid addition salts with inorganic acids such as hydrochloric acid, nitric acid, hydrobromic acid and sulfuric acid; salts with an aliphatic monocarboxylic acid and dicarboxylic acid, a hydroxy alkanoic acid, a hydroxy dialkanoic acid and an amino acid; and salts derived from non-toxic organic acids such as an aromatic acid, and an aliphatic or an aromatic sulfonic acid. Examples of the acid addition salt include hydrochloride, hydrobromide, nitrate, sulfate, hydrogen sulfate, monohydrogen phosphate, dihydrogen phosphate, acetate, propionate, tartrate, oxalate, malonate, succinate, fumarate, maleate, mandelate, benzoate, phthalate, methanesulfonate, benzenesulfonate, toluenesulfonate, citrate, lactate, malate, and glycolate.

The above-described acid addition salts are significant as pharmacologically acceptable pharmaceutical compositions. It is believed that they are advantageous in preparing a pharmaceutical composition and are useful when administrated to an organism because of excellent dispersing ability and absorption ability.

A pharmaceutical composition comprising the compound of the present invention as an effective ingredient can be administrated orally or non-orally (i.e., intravenous administration, intramuscular administration, subcutaneous administration, rectum administration, percutaneous administration) to human being and animals other than human being. Accordingly, a pharmaceutical composition comprising the compound (I) as an effective ingredient is formulated to an appropriate form corresponding to an administration route.

Specifically, examples of the orally administrated agent include tabella, capsule agent, powder, granule and syrup. Examples of the non-orally administrated agent include injection agents such as intravenous and intramuscular agent, rectum administrating agents, suppositories consists of oils and fats and aqueous suppositories.

These various kinds of preparations can be produced according to an ordinary method using currently used agents such as a shaping agent, a decaying agent, a binding agent, a lubricant and a coloring agent. Examples of the shaping agent include lactose, glucose, corn starch, sorbitol and crystalline cellulose. Examples of the decaying agent include starch, sodium alginate, gelatin powder, calcium carbonate, calcium citrate and dextrin. Examples of the binding agent include dimethyl cellulose, polyvinyl alcohol, polyvinyl ether, methyl cellulose, ethyl cellulose, gum arabic, gelatin, hydroxypropyl cellulose and polyvinyl pyrrolidone. Examples of the lubricant include talc, magnesium stearate, polyethylene glycol and a hardening plant oil. The above-described injection agents can be also produced by optionally adding a buffer, a pH controlling agent, a stabilizer or the like.

Although the content of the compound (I) according to the present invention in a pharmaceutical composition differs depending upon the form of a preparation, it is usually 0.1 to 50% by weight, preferably 0.1 to 20% by weight of the composition. An amount to be administrated is optionally determined corresponding to each case by taking an age, sex, a kind of disease, and a state of a disease into consideration. However, usually, an administration amount to an adult is 0.1 to 100 mg, preferably 0.1 to 30 mg a day, which is administrated once or in portionwise a day.

BEST MODE FOR CARRYING OUT OF INVENTION

The present invention will be further described in detail by, but by no means limited to, the following Examples and Test Examples, wherein the description of "the compound of the present invention" means the compound (I).

EXAMPLES

Synthesis Example 1

(RS)-2a-methoxycarbonylmethyl)-2a,3,4,5-tetrahydro-1H-benz[cd]indol-2-one (RS)-2a,3,4,5-tetrahydro-1H-benz[cd]indol-2-one (8.65 g, 50 mmol) was dissolved in anhydrous N,N,-dimethylformamide (70 ml). Then, 60% sodium hydride (1.90 g, 48 mmol) was added thereto and the resulting mixture was stirred at 25° C. for 1 hour. Successively the reaction mixture obtained was cooled to −10° C., and methyl bromoacetate (4.65 ml, 50 mmol) was added thereto. The resulting mixture was stirred for further 2 hours. Ethyl acetate and water were added thereto to extract the reaction product. The ethyl acetate solution was washed with saturated saline solution and then dried over anhydrous sodium sulfate, and then the solvent was evaporated under reduced pressure to obtain a reaction product. Thereafter, diisopropyl ether was added to the resulting reaction product to crystallized the same. Thus, the above-described object compound was obtained in an amount of 7.99 g (yield 62%). $^1$H-NMR (CDCl$_3$)δ 7.70 (1H, br s), 7.14 (1H, t), 6.81 (1H, d), 6.70 (1H, d), 3.53 (3H, s), 2.85 (2H, dd), 2.83 (1H, m), 2.70 (1H, m), 2.20 (2H, m), 1.87 (1H, m), 1.28 (1H, m); MW 245.28 (C$_{14}$H$_{15}$NO$_3$); mass spectrum EIMS m/z 245 (M)$^+$ Synthesis Example 2 (Intermediate of the Present Invention)

(S)-2a-carboxymethyl-2a,3,4,5-tetrahydro-1H-benz[cd]indol-2-one•(R)-phenethylamine Salt (RS)-2a-(methoxycarbonylmethyl)-2a,3,4,5-tetrahydro-1H-benz[cd]indol-2-one (1.3 g, 5.3 mmol) was dissolved in methanol (10 ml). Then, 1N sodium hydroxide solution (5.5 ml, 5.4 mmol) was added thereto and the resulting mixture was reacted at 25° C. for 2 days. Successively, ethyl acetate and aqueous hydrochloric acid were added thereto to extract a reaction product. The ethyl acetate solution was washed with saturated saline solution and then dried over anhydrous sodium sulfate, and then the solvent was evaporated under reduced pressure to obtain a product, which was dissolved in acetone (50 ml). Then, (R)-phenethylamine (360 mg, 3 mmol) was added thereto to effect crystallization, followed by filtration. Thus, 814 mg (yield 44%) of the crystal was obtained. Mw 352.43 (C$_{21}$H$_{24}$N$_2$O$_3$); [α]$_D$+22.1° (c=1, methanol)

Synthesis Example 3 (Intermediate of the Present Invention)

(S)-2a-carboxymethyl-2a,3,4,5-tetrahydro-1H-benz[cd]indol-2-one

To (S)-2a-carboxymethyl-2a,3,4,5-tetrahydro-1H-benz[cd]indol-2-one•(R)-phenethylamine salt (1.76 g, 5 mmol) was added water (30 ml) and 1N hydrochloric acid solution (15 ml), and the resulting reaction mixture was stirred and the deposited crystal was filtered. Thus, 1.14 g (yield 98%) of the crystal was obtained.

$^1$H-NMR (CDCl$_3$)δ 8.61 (1H, br s), 7.13 (1H, t), 6.87 (1H, dd), 6.60 (1H, d), 3.41 (1H, m), 3.08 (1H, d), 2.91 to 2.81 (2H, m), 2.45 (1H, d), 1.92 (3H, m), 1.65 (1H, m); MW 231.25 (C$_{13}$H$_{13}$NO$_3$); mass spectrum EIMS m/z 231 (M)$^+$; [α]$_D$+44.1° (c=1, 80% aqueous acetone)

Synthesis Example 4

(RS)-2a-(2-ethoxycarbonylethyl)-2a,3,4,5-tetrahydro-1H-benz[cd]indol-2-one (RS)-2a,3,4,5-tetrahydro-1H-benz[cd]indol-2-one(3.46 g, 20 mmol) was dissolved in anhydrous N,N,-dimethylformamide (20 ml). Then, 60% sodium hydride (0.8 g, 20 mmol) was added thereto and the resulting mixture was stirred at room temperature for 1 hour. Successively the reaction mixture obtained was cooled to −20° C., and ethyl 3-bromo propionate (2.55 ml, 20 mmol) was added thereto. The resulting mixture was stirred at room temperature for further 1 hour. Ethyl acetate and water were added thereto to extract a reaction product. The ethyl acetate solution was washed with saturated saline solution and then dried over anhydrous sodium sulfate, and then the solvent was evaporated under reduced pressure to obtain a reaction product. Thereafter, diisopropyl ether was added to the resulting reaction product to crystallized the same. Thus, the above-described object compound was obtained in an amount of 3.80 g (yield 70%).

$^1$H-NMR (CDCl$_3$) δ 7.57 (1H, br s), 7.12 (1H, t), 6.80 (1H, d), 6.68 (1H, d), 3.98 (2H, q), 2.87 (1H, m), 2.64 (1H, m), 2.33 (1H, m), 2.14 (5H, m), 1.84 (1H, m), 1.38 (1H, m), 1.18 (3H, t); MW 273.33 (C$_{16}$H$_{19}$NO$_3$); mass spectrum EIMS m/z 273 (M)$^+$

Synthesis Example 5 (Intermediate of the Present Invention)

(S)-2a-(2-carboxyethyl)-2a,3,4,5-tetrahydro- 1H-benz[cd]indol-2-one•(R)-phenethylamine Salt (RS)-2a-(2-ethoxycarbonylethyl)-2a,3,4,5-tetrahydro-1H-benz[cd]indol-2-one (19.07 g, 70 mmol) was dissolved in methanol (250 ml). Then, 1N sodium hydroxide solution (70 ml, 70 mmol) was added thereto and the resulting mixture was reacted at 25° C. for 18 hours. Successively, ethyl acetate and aqueous hydrochloric acid were added thereto to extract a reaction product. The ethyl acetate solution was washed with saturated saline solution and then dried over anhydrous sodium sulfate, and then the solvent was evaporated under reduced pressure to obtain a reaction product (20 g), which was then dissolved in the mixture of ethyl acetate (150 ml) and acetone (150 ml). To the resulting solution was added(R)-phenethylamine (7.2 g, 60 mmol) to effect crystallization, followed by filtration. Thus, 8.54 g (yield 33%) of the crystal was obtained. MW 366.46 (C$_{22}$H$_{26}$N$_2$O$_3$); [α]$_D$+42.2° (c=1, methanol)

Synthesis Example 6 (Intermediate of the Present Invention)

(S)-2a-(2-carboxyethyl)-2a,3,4,5-tetrahydro-1H-benz[cd]indol-2-one

To (S)-2a-(2-carboxyethyl)-2a,3,4,5-tetrahydro-1H-benz[cd]indol-2-one•(R)-phenethylamine salt (1.83 g, 5 mmol) was added water (30 ml) and 1N hydrochloric acid solution (15 ml), and the resulting reaction mixture was stirred and the deposited crystal was filtered. Thus, 1.12 g (yield 91%) of the crystal was obtained.

MW 245.28 (C$_{14}$H$_{15}$NO$_3$); $^1$H-NMR (CDCl$_3$) δ 8.57 (br s), 7.12 (1H, t), 6.79 (1H, d), 6.71 (1H, d), 2.86 (1H, m), 2.65 (1H, m), 2.35 to 2.08 (7H, m), 1.86 (1H, m), 1.38 (3H, m); mass spectrum EIMS m/z 245 (M)$^+$; [α]$_D$+79.9° (c=1, chloroform)

Synthesis Example 7

(RS)-2a-(3-ethoxycarbonylpropyl)-2a,3,4,5-tetrahydro-1H-benz[cd]indol-2-one (RS)-2a,3,4,5-tetrahydro-1H-benz[cd]indol-2-one (8.65 g, 50 mmol) was dissolved in anhydrous N,N,-dimethylformamide (70 ml). Then, 60% sodium hydride (2.0 g, 50 mmol) was added thereto and the resulting mixture was stirred at room temperature for 1 hour. Successively the reaction mixture obtained was cooled to −20° C., and ethyl 3-bromobutyrate (7.15 ml, 50 mmol) was added thereto. The resulting mixture was stirred at room temperature for further 18 hours. Ethyl acetate and water were added thereto to extract a reaction product. The ethyl acetate solution was washed with saturated saline solution and then dried over anhydrous sodium sulfate, and then the solvent was evaporated under reduced pressure to obtain a reaction product. Thereafter, diisopropyl ether was added to the resulting reaction product to crystallized the same. Thus, the above-described object compound was obtained in an amount of 8.01 g (yield 56%).

$^1$H-NMR (CDCl$_3$) δ 7.71 (1H, br s), 7.11 (1H, t), 6.81 (1H, d), 6.68 (1H, d), 4.07 (2H, q), 2.82 (1H, m), 2.70 (1H, m), 2.21 (2H, t), 2.12 (2H, m), 1.84 (3H, m), 1.65 (1H, m), 1.38 (2H, t), 1.21 (3H, t); MW 287.36 (C$_{17}$H$_{21}$NO$_3$); mass spectrum EIMS m/z 287 (M)$^+$

Synthesis Example 8

(RS)-2a-(3-carboxypropyl)-2a,3,4,5-tetrahydro-1H-benz[cd]indol-2-one (RS)-2a-(3-ethoxycarbonylpropyl)-2a,3,4,5-tetrahydro-1H-benz[cd]indol-2-one (6.20 g, 21.6 mmol) was dissolved in dimethoxyethane (70 ml). Then, 1N sodium hydroxide solution (22 ml, 22 mmol) was added thereto to effect a reaction at 25° C. for 18 hours. Successively the resulting solution was concentrated and aqueous hydrochloric acid was added to the residue obtained to effect crystallization, followed by filtration. Thus, the crystal was obtained in an amount of 5.45 g (yield 97%). MW 259.30 (C$_{15}$H$_{17}$NO$_3$); mass spectrum EIMS m/z 259(M)$^+$

Synthesis Example 9 (Intermediate of the Present Invention)

(S)-2a-(3-carboxypropyl)-2a,3,4,5-tetrahydro-1H-benz[cd]indol-2-one•(S)-valinol Salt (RS)-2a-(3-carboxypropyl)-2a,3,4,5-tetrahydro-1H-benz[cd]indol-2-one (12.47 g, 48.1 mmol) was dissolved in dimethoxyethane (250 ml). Then, (S)-valinol (5.0 g, 48.5 mmol) was added thereto and dissolved at 40° C., which was further allowed to stand at 20° C. to deposit the crystal, followed by filtration. Thus, the crystal was obtained in the amount of 6.37 g (yield 37%).

$^1$H-NMR (CDCl$_3$) δ 8.93 (1H, s), 7.11 (1H, t), 6.80 (1H, d), 6.72 (1H, d), 2.84 (1H, m), 2.64 (1H, ddd), 2.19 (4H, m), 1.86 (3H, m), 1.65 (1H, m), 1.38 (2H, m); MW 362.47 (C$_{20}$H$_{30}$N$_2$O$_4$); [αC]$_D$+37.2° (c=1, methanol)

Synthesis Example 10 (Intermediate of the Present Invention)

(S)-2a-(3-carboxypropyl)-2a,3,4,5-tetrahydro-1H-benz[cd]lindol-2-one (S)-2a-(3-carboxypropyl)-2a,3,4,5-tetrahydro-1H-benz[cd]indol-2-one•(S)-valinolate (36.2 g, 10 mmol) was dissolved in water (50 ml). Then, 5N hydrochloric acid was added thereto to effect crystallization. The deposited crystal obtained by filtration was 2.28 g (yield 88%).

$^1$H-NMR (CDCl$_3$) δ 7.42 (1H, s), 7.11 (1H, t), 6.80 (1H, d), 6.67 (1H, d), 3.62 (3H, s), 2.84 (1H, m), 2.64 (1H, ddd), 2.23 (2H, dt), 2.10 (2H, m), 1.84 (3H, m), 1.66 (1H, m) 1.66 (1H, m); MW 259.30 (C$_{15}$H$_{17}$NO$_3$); mass spectrum EIMS m/z 259 (M)$^+$; [α]$_D$+53.3° (c=1, chlroform)

Synthesis Example 11 (Intermediate of the Present Invention)

(S)-2a-(3-methoxycarbonylpropyl)-2a,3,4,5-tetrahydro-1H-benz[cd]indol-2-one (S)-2a-(3-carboxypropyl)-2a,3,4,5-tetrahydro-1H-benz[cd]indol-2-one (7.00 g, 27 mmol) was dissolved in methanol (200 ml). Then, 36% hydrochloric acid 0.1 ml was added thereto and stirred at room temperature for two days. The solvent was evaporated from the reaction mixture, and ethyl acetate and water were added to the resulting residue. A reaction product was extracted with ethyl acetate, and the extracted product was washed with saturated saline solution, successively dried over anhydrous sodium sulfate, followed by evaporating the solvent. The resulting product was crystallized from diisopropyl ether, whereby 6.89 g (yield 93%) of the above-described object compound could be obtained.

$^1$H-NMR (CDCl$_3$) δ 8.67 (1H, s), 7.09 (1H, t), 6.79 (1H, d), 6.68 (1H, d), 3.52 (2H, t), 2.84 (1H, m), 2.63 (1H, ddd), 2.25 (H, br s), 2.11 (2H, m), 1.83 (3H, m), 1.39 (4H, m), 1.10 (1H, m); MW 273.33 (C$_{16}$H$_{19}$NO$_3$); mass spectrum EIMS m/z 259 (M)$^+$; [α]$_D$+56.6° (c=1, chlroform)

Synthesis Example 12 (Intermediate of the Present Invention)

(S)-2a-(4-hydroxybutyl)-2a,3,4,5-tetrahydro-1H-benz[cd]indol-2-one (S)-2a-(3-methoxycarboxypropyl)-2a,3,4,5-tetrahydro-1H-benz[cd]indol-2-one (4.1 g, 15 mmol) was dissolved in dimethoxyethane (60 ml). Then, tetrahydrofuran solution of 1.6 M lithiumborohydride (9.0 ml, 18 mmol) was added to the resulting solution and stirred at room temperature for two days. The solvent was evaporated from the reaction mixture, and ethyl acetate, water and hydrochloric acid (1N) were added to the resulting residue. The reaction product was extracted with ethyl acetate, and the extracted product was washed with saturated saline solution, successively dried over anhydrous sodium sulfate, followed by evaporating the solvent. The resulting product was separated and purified by means of silica gel column chromatography, whereby 2.15 g (yield 58%) of the above-described object compound could be obtained.

$^1$H-NMR (CDCl$_3$) δ 7.44 (1H, s), 7.12 (1H, t), 6.81 (1H, d), 6.68 (1H, d), 3.31 (2H, t), 2.85 (1H, m), 2.65 (1H, ddd), 2.13 (2H, m), 1.81 (5H, m), 1.42 (2H, m), 1.22 (1H, m); MW 245.32 (C$_{15}$H$_{19}$NO$_3$); mass spectrum EIMS m/z 245 (M)$^+$; [α]$_D$+34.3° (c=1, chlroform)

Synthesis Example 13 (Intermediate of the Present Invention)

(S)-2a-(4-bromobutyl)-2a,3,4,5-tetrahydro-1H-benz[cd]indol-2-one (S)-2a-(4-hydroxybutyl)-2a,3,4,5-tetrahydro-1H-benz[cd]indol-2-one (1.96 g, 8.0 mmol) was dissolved in acetonitrile (50 ml). Then, carbon tetrabromide (3.31 g, 10.0 mmol) and triphenylphosphine (2.72 g, 9.6 mmol) were added to the resulting solution and stirred at room temperature for four hours. The solvent was evaporated from the reaction mixture, and ethyl acetate, water and hydrochloric acid (1N) were added to the resulting residue. The reaction product was extracted with ethyl acetate, and the extracted product was washed with saturated saline solution, successively dried over anhydrous sodium sulfate, followed by evaporating the solvent. The resulting product was separated and purified by means of silica gel column chromatography, whereby 2.40 g (yield 97%) of the above-described object compound could be obtained.

$^1$H-NMR (CDCl$_3$) δ 1.17–1.28 (1H, m), 1.32–1.51 (2H, m), 1.72–1.90 (5H, m), 2.06–2.19 (2H, m), 2.60–2.70 (1H, m), 2.80–2.89 (1H, m), 3.30 (2H, t, J=7.0 Hz), 6.67 (1H,d, J=7.4 Hz), 6.81 (1H, d, J=7.8 Hz), 7.12 (1H, dd), 7.34 (1H, br s); MW 308.22 (C$_{15}$H$_{18}$BrNO); mass spectrum EIMS m/z 307:309=1:1 (M)$^+$; [α]$_D$+41.6° (c=0.31, chlroform)

Synthesis Example 14 (Compound of the Present Invention)

(S)-2a-(4-(4-(2-methoxyphenyl)piperazinyl)butyl)-2a,3,4,5-tetrahydro-1H-benz[cd]indol-2-one (S)-2a-(4-bromobutyl)-2a,3,4,5-tetrahydro-1H-benz[cd]indol-2-one (308 mg, 1.0 mmol), 4-(2-methoxyphenyl)piperazine (415 mg, 2.1 mmol) and potassium carbonate (280 mg, 2.0 mmol) in anhydrous N,N-dimethylformamide (10 ml) were stirred at room temperature for 18 hours. Then, ethyl acetate (80 ml) was added to the resulting reaction mixture, which was washed with water and saturated saline solution, successively dried over anhydrous sodium sulfate, followed by evaporating the solvent under reduced pressure. The resulting product was separated and purified by means of silica gel column chromatography, whereby 350 mg (yield 84%) of the above-described object compound could be obtained.

$^1$H-NMR (CDCl$_3$) δ 7.42 (1H, br s), 7.12 (1H, dd), 6.88–7.00 (3H, m), 6.84 (1H, d), 3.85 (3H, s), 3.05 (4H, br s), 2.80–2.90 (1H, m), 2.54–2.68 (5H, m), 2.25–2.38 (2H, m), 2.07–2.20 (2H, m), 1.76–1.92 (3H, m), 1.26–1.51 (4H, m), 1.04–1.15 (1H, m); MW 419.57 (C$_{26}$H$_{33}$N$_3$O$_2$);

To form hydrochloride, the free base isolated was dissolved in hydrochloric acid-saturated methanol and dried. MW 456.03 (C$_{26}$H$_{34}$ClN$_3$O$_2$); mass spectrum EIMS m/z 419(M-HCl)$^+$; [α]$_D$+14.8° (c=1, methanol)

Synthesis Example 15 (Compound of the Present Invention)

(S)-2a-(4-(4-phenyl-1,2,3,6-tetrahydropyridin)-1-ylbutyl)-2a,3,4,5-tetrahydro-1H-benz[cd]indol-2-one (S)-2a-(4-bromobutyl)-2a,3,4,5-tetrahydro-1H-benz[cd]indol-2-one (132 mg, 0.43 mmol), 4-phenyl-1,2,3,6-tetrahydropyridine hydrochloride (100 mg, 0.51 mmol) and potassium carbonate (207 mg, 1.5 mmol) in N,N-dimethylformamide (2 ml) were stirred at room temperature for 2 days. Then, ethyl acetate (80 ml) was added to the resulting reaction mixture, which was washed with water and saturated saline solution, successively dried over anhydrous sodium sulfate, followed by evaporating the solvent under reduced pressure. The resulting product was separated and purified by means of silica gel column chromatography, whereby 41 mg (yield 84%) of the above-described object compound could be obtained.

$^1$H-NMR (CDCl$_3$) δ 7.54 (1H, br s), 7.19–7.38 (5H, m), 7.11 (1H, dd), 6.80 (1H, d), 6.67 (1H, d), 6.02 (1H, s), 3.10 (2H, dd), 2.80–2.89 (1H, m), 2.60–2.69 (3H, m), 2.50–2.57 (5H, m), 2.29–2.42 (2H,m), 2.07–2.20 (2H, m), 1.77–1.93 (3H,m) 1.25–1.55 (4H,m), 1.04–1.06 (1H,m); MW 386.54 (C$_{26}$H$_{30}$N$_2$O); mass spectrum EIMS m/z 386(M)$^+$, [α]$_D$+ 22.4° (c=1, methanol)

Synthesis Example 16 (Compound of the Present Invention)

(S)-2a-(4-(4-((1R)-1,2,3,4-tetrahydronaphthalen-1-yl)piperazin-1-yl)butyl)-2a,3,4,5-tetrahydro-1H-benz[cd]indol-2-one (S)-2a-(4-bromobutyl)-2a,3,4,5-tetrahydro-1H-benz[cd]indol-2-one (2 g, 6.49 mmol), (R)-tetrahydronaphthylpiperazine•oxalate (2.98 g, 9.73 mmol) and potassium carbonate (7.18 g, 51.95 mmol) were suspended in dimethylformamide (40 ml), and stirred at room temperature for 10 hours. The resulting reaction mixture was evaporated under reduced pressure to obtain residue to which dichloromethane was added. The dichlormethane solution thus obtained was washed with water, successively dried over anhydrous sodium sulfate, followed by evaporating the solvent under reduced pressure, whereby an oily product was obtained. The product obtained was purified by means of silica gel column chromatography, and crystallized from hexane and ethyl acetate, whereby 2.2 g (yield 76%) of the above-described object compound could be obtained.

$^1$H-NMR (CDCl$_3$) δ 0.98–1.12 (1H, m), 1.25–1.48 (4H, m), 1.63–1.72 (3H, m), 1.73–2.00 (5H, m), 2.04–2.17 (2H, m), 2.17–2.30 (2H, m), 2.32–2.55 (5H, m), 2.55–2.90 (6H, m) 3.75–3.82 (1H, m), 6.68 (1H, d, J=7.7 Hz), 6.82 (1H, d, J=7.7 Hz) 7.02–7.16 (3H, m), 7.33 (1H, s), 7.67 (1H, d, J=8.52 Hz); MW 443.63 (C$_{29}$H$_{37}$N$_{3}$O); mass spectrum EIMS m/z 443(M)$^+$, [α]$_D$-16.9° (c=1, chloroform)

Synthesis Example 17 (Compound of the Present Invention)

(S)-2a-[4-(9-dimethylcarbamoyl-2,3,4,9-tetrahydro-1H-pyrido[3,4-b]indol-2-yl)-butyl]-2a,3,4,5-tetrahydro-1H-benz[cd]indol-2-one To 1.4 ml of DMF solution of (S)-2a-(4-bromobutyl)-2a,3,4,5-tetrahydro-1H-benz[cd]indol-2-one (65 mg, 0.21 mmol) and 9-dimethylcarbamoyl-2,3,4,9-tetrahydro-1H-pyrido-1H-pyrido[3,4-b]indole hydrochloride (71 mg, 0.25 mmmol) was added potassium carbonate (87 mg, 0.75 mmol). The resulting mixture was stirred at room temperature for 2 days. The reaction mixture obtained was extracted with ethyl acetate and washed with water. After drying (Na$_2$SO$_4$), the solvent was evaporated under reduced pressure to obtain an oily product. The product obtained was purified by means of silica gel column chromatography (eluted with 20 ml; chloroform-methanol=10:1), and recrystallized from ethyl acetate-diisopropyl ether, whereby 86 mg (yield 86%) of the above-described object compound could be obtained.

$^1$H-NMR (CDCl$_3$) δ 1.10 (1H, m), 1.33 (2H, m), 1.52 (2H, m), 1.83 (3H, m), 2.10 (2H, m), 2.51 (2H, m), 2.62 (1H, ddd), 2.81 (5H, m), 3.03 (6H, s), 3.71 (2H, s), 6.65 (1H, d), 6.77 (1H, d), 7.07 (2H, t), 7.11–7.22 (3H, m), 7.42 (1H, d), 8.48 (1H, s); mass spectrum TSP m/z 471(M+H)$^+$

Synthesis Example 18 (Compound of the Present Invention)

(S)-2a-(4-(1,2,3,4-tetrahydroisoquinolin-2-yl)-butyl)-2a,3,4,5-tetrahydro-1H-benz[cd]indol-2-one (S)-2a-(4-bromobutyl)-2a,3,4,5-tetrahydro-1H-benz[cd]indol-2-one (120 mg, 0.40 mmol), 1,2,3,4-tetrahydroisoquinoline (59 mg, 0.44 mmol), and potassium carbonate (83 mg, 0.60 mmol) in anhydrous N,N-dimethylformamide (1 ml) were stirred at room temperature for 2 days. To the reaction mixture obtained was added ethyl acetate (80 ml), which was then washed with water and saturated saline solution. After drying with anhydrous sodium sulfate, the solvent was evaporated under reduced pressure to obtain a product. The product obtained was separated and purified by means of silica gel column chromatography, whereby 150 mg (0.40 mmol, yield 100%) of the above-described object compound could be obtained.

$^1$H-NMR (CDCl$_3$) δ 1.05–1.17 (1H, m), 1.30–1.42 (2H, m), 1.42–1.59 (2H, m), 1.76–1.94 (3H, m), 2.06–2.20 (2H, m), 2.35–2.46 (2H, m), 2.59–2.69 (3H, m), 2.79–2.89 (3H, m), 3.55 (2H, s), 6.66 (1H, d, J=7.8 Hz), 6.80 (1H, d, J=7.8 Hz), 6.97 (1H, dd), 7.05–7.17 (4H, m), 7.58 (1H,br s); MW 360.50 (C$_{24}$H$_{28}$N$_2$O); mass spectrum EIMS m/z 360(M)$^+$ To form hydrochloride, the free base isolated was dissolved in hydrochloric acid-saturated methanol and dried. MW (C$_{24}$H$_{28}$ClN$_2$O)396.96; mass spectrum EIMS m/z 360 (M-HCl)$^+$, [α]$_D$+9.5° (c=1, methanol)

Synthesis Example 19 (Compound of the Present Invention)

(S)-2a-(4-(3-methyl-4,5,6,7-tetrahydro thieno[3,2-c] pyridin-5-yl)butyl)-2a,3,4,5-tetrahydro-1H-benz[cd]indol-2-one A synthesis was effected according the same manner as that of Synthesis Example 14, except for using 3-methyl-4,5,6,7-tetrahydro thieno[3,2-c]pyridine instead of 4-(2-methoxyphenyl)piperazine. Thus, the above-described object compound could be obtained (yield 78%).

$^1$H-NMR (CDCl$_3$) δ 1.05–1.17 (1H, m), 1.31–1.56 (4H, m), 1.78–1.93 (3H, m), 2.03–2.19 (5H, m), 2.40–2.52 (2H, m) 2.60–2.71 (3H, m), 2.79–2.89 (3H, m), 3.34 (2H, s), 6.65–6.67 (2H, m), 6.80 (1H, d, J=7.6 Hz), 7.11 (1H, d, J=7.8 Hz), 7.23 (1H,br s); MW 380.55 (C$_{23}$H$_{28}$N$_2$OS); mass spectrum EIMS m/z 380(M)$^+$

Synthesis Example 20 (Compound of the Present Invention)

(S)-2a-(4-(2,3-dimethyl-4,5,6,7-tetrahydro thieno[3,2-c] pyridin-5-yl)butyl)-2a,3,4,5-tetrahydro-1H-benz[cd]indol-2-one A synthesis was effected according the same manner as that of Synthesis Example 14, except for using 2,3-dimethyl-4,5,6,7-tetrahydro thieno[3,2-c]pyridine instead of 4-(2-methoxyphenyl)piperazine. Thus, the above-described object compound could be obtained (yield 89%).

$^1$H-NMR (CDCl$_3$) δ 1.04–1.16 (1H, m), 1.30–1.56 (4H, m), 1.77–1.93 (6H, m), 2.05–2.19 (2H, m), 2.27 (3H, s), 2.40–2.50 (2H, m), 2.60–2.70 (3H, m), 2.71–2.76 (2H, m), 2.80–2.89 (1H, m), 3.29 (2H, s), 6.66 (1H, d, J=7.6 Hz), 6.80 (1H, d, J=7.8 Hz), 7.11 (1H,dd), 7.22 (1H,br s); MW 394.58 (C$_{24}$H$_{30}$N$_2$OS); mass spectrum EIMS m/z 394 (M)$^+$

Synthesis Example 21 (Compound of the Present Invention)

(S)-2a-(4-(2-methyl-4,5,6,7-tetrahydro thieno[3,2-c] pyridin-5-yl)butyl)-2a,3,4,5-tetrahydro-1H-benz[cd]indol-2-one A synthesis was effected according the same manner as that of Synthesis Example 14, except for using 2-methyl-4,5,6,7-tetrahydro thieno[3,2-c]pyridine instead of 4-(2-methoxyphenyl)piperazine (yield 51%).

$^1$H-NMR (CDCl$_3$) δ 1.03–1.16 (1H, m), 1.29–1.53 (4H, m), 1.76–1.92 (3H, m), 2.06–2.18 (2H, m), 2.36–2.47 (5H, m), 2.59–2.89 (6H, m), 3.38 (2H, s), 6.33 (1H, s), 6.65 (1H, d, J=7.8 Hz), 6.80 (1H, d, J=7.8 Hz), 7.09–7.14 (2H, m); MW 380.55 (C$_{23}$H$_{28}$N$_2$OS); mass spectrum EIMS m/z 380 (M)$^+$

Synthesis Example 22 (Compound of the Present Invention)

(S)-2a-(4-(9-methylcarbamoylmethyl-2,3,4,9-tetrahydro-1H-pyrido[3,4-b]indol-2-yl)butyl)-2a,3,4,5-tetrahydro-1H-benz[cd]indol-2-one 9-methylcarbamoylmethyl-2,3,4,9-tetrahydro-1H-pyrido[3,4-b]indole•trifluoroacetate (450 mg, 1.26 mmol) and (S)-(4-bromobutyl)-2a,3,4,5-tetrahydro-1H-benz[cd]indol-2-one (308 mg, 1.0 mmol) were dissolved in dimethylformamide (5 ml). Then triethylamine(0.9 ml, 6 mmol) was added thereto. The resulting solution was reacted at room temperature for 3 days. To the reaction mixture obtained was added ethyl acetate (50 ml), which was then washed with water (50 ml×2) and saturated saline solution, successively dried with anhydrous sodium sulfate. The ethyl acetate solution was concentrated under reduced pressure to obtain a crude reaction product, which was purifiedbymeans of silica gel column chromatography, whereby 376 mg (yield 80%) of the above-described object compound could be obtained.

$^1$H-NMR (CDCl$_3$) δ 1.14 (1H, m), 1.31–1.40 (2H, m), 1.48–1.55 (2H, m), 1.78–1.94 (3H, m), 2.06–2.14 (2H, m), 2.55–2.59 (2H, m), 2.64 (1H, m), 2.69 (3H, d), 2.79 (5H, m), 3.52 (2H, s), 4.61 (2H, s), 5.46 (1H, q), 6.67 (1H, d, J=7.8 Hz), 6.80 (1H, d, J=7.8 Hz), 7.10–7.20 (4H, m), 7.50 (1H, d, J=7.8 Hz), 7.60(1H, brs); MW 417.01 (C$_{29}$H$_{34}$N$_4$O$_2$); mass spectrum EIMS m/z 470 (M)$^+$ Synthesis Example 23 (Compound of the Present Invention)

(S)-2a-(4-(9-(2-hydroxy)ethyl-2,3,4,9-tetrahydro-1H-pyrido[3,4-b]indol-2-yl)butyl)-2a,3,4,5-tetrahydro-1H-benz[cd]indol-2-one (2-acetoxy)ethyl-2,3,4,9-tetrahydro-1H-pyrido[3,4-b]indole•trifluoroacetate (230 mg, 0.73 mmol) and (S)-4-bromobutyl)-2a,3,4,5-tetrahydro-1H-benz[cd]indol-2-one (185 mg, 0.6 mmol) were dissolved in dimethylformamide (5 ml). Then anhydrous potassium carbonate (280 mg, 2 mmol) was added thereto. The resulting reaction mixture was stirred at room temperature for 2 days. To the reaction mixture obtained was added ethyl acetate (50 ml), which was then washed with water (50 ml×2) and saturated saline solution, successively dried with anhydrous sodium sulfate. The ethyl acetate solution was concentrated under reduced pressure. To the resulting product were added methanol (30 ml) and triethylamine (3 ml), which was heated at 50° C. for 5 hours and then subjected to concentration again under reduced pressure to obtain a crude reaction product. Silica gel column chromatography was applied to purify the same, whereby 246 mg (yield 76%) of the above-described object compound could be obtained.

$^1$H-NMR (CDCl$_3$) δ 1.10 (1H, m), 1.26 (2H, m), 1.34 (2H, m), 1.42 (2H, m), 1.51 (2H, m), 1.85 (4H, m), 2.10 (3H, m), 2.50 (2H, m), 2.64 (1H, m), 2.83 (1H, m), 3.65 (2H, q), 3.83 (1H, t), 4.09 (2H, t), 6.64 (1H,d J=7.8 Hz), 6.80 (1H, d, J=7.8 Hz), 7.10 (3H, m), 7.25 (1H, d), 7.44 (1H, d), 7.85 (1H, br s); MW 443.58 (C$_{28}$H$_{33}$N$_3$O$_2$); mass spectrum EIMS m/z 443 (M)$^+$ Test Example 1

5-HT$_7$ Receptor-binding Assay

Membranes from culture cells expressing cloned human 5-HT$_7$ receptor were harvested and homogenized in 50 mM Tris-HCl assay buffer (pH 7.4) containing 10 mM MgCl$_2$ and 0.5 mM EDTA with a potter-type homogenizer, and the suspension was centrifuged at 4° C., 39,000×g for 20 minutes. The resulting pellet was resuspended in the assay buffer at a proportion of 1 ml per an amount of a piece of culture petri dish having a diameter of 10 cm, and homogenized again.

The binding assay was performed as follows, 100 μl of the final suspension was added to 1nM[$^3$H]-5CT (carboxyamido tryptamine) and 1 to 1000 nM test compounds (compounds of the present invention of Synthesis Examples 1 to 26) with the final volumes of 300 μl and incubated at 37° C. for 30 minutes. The incubation was terminated by rapid filtration through GB/B filter, washed with 6 ml of ice-cold 50 mM Tris-HCl buffer (pH 7.4). The bound radioactivity was determined by liquid scintillation counter. While, non-specific binding was determined in the presence of 10 μM metergoline. The specific binding was calculated from the bound radioactivity after subtraction of non-specific binding. From the inhibition curves of each compound, IC$_{50}$ was determined, from which the inhibition dissociation constant (Ki) of each compound was calculated. The results are shown in Table 1.

Test Example 2

5-HT$_2$ Receptor-binding Assay

Rat cerebral cortex was homogenized in 10 volumes of 0.32 M sucrose solution. The supernatant obtained by centrifuging at 900×g for 10 minutes was further centrifuged at 11,500×g for 20 minutes. The pellet was resuspended in 50 mM Tris-HCl buffer (pH 7.4) and then centrifuged at 39,900×g for 20 minutes. The final pellet was used a P2 fraction.

P2 fraction was incubated in 50 mM tris-HCl buffer (pH 7.4) containing 1 nM [$^3$H]ketanserin and the compound of the present invention at 37° C. for 15 minutes and terminated by rapid filtration through GF/B filters. The bound radioactivity was determined by liquid scintillation counter. While, non-specific binding was determined in the presence of 10 μM ketanserin. Thus, the specific binding was calculated from the bound radioactivity after the subtraction of non-specific binding. From the inhibition curves of each compound, IC$_{50}$ was determined, from which the inhibition dissociation constant (Ki) of each compound was calculated.

Ratios of Ki (5-HT$^2$) with Ki (5-HT$_7$) obtained from Test Example 1 are shown in Table 1. It is apparent from Table 1 that the compounds of the present invention are bound with 5-HT$_7$ receptor more selectively.

TABLE 1

| | Receptor Binding Affinity Ki Value (nM) | | |
|---|---|---|---|
| Test Compound | Ki Value (5-HT$_7$) | Ki Value (5-HT$_2$) | Selectivity |
| Compound of Synthesis Example 14 | 1.7 | 84 | 49 |
| Racemic Mixture of the Above Compound | 8.9 | 60 | 7 |
| Compound of Synthesis Example 15 | 1.3 | 42 | 32 |
| Racemic Mixture of the Above Compound | 9.0 | 92 | 10 |
| Compound of Synthesis Example 17 | 4.0 | >1000 | >250 |
| Racemic Mixture of the Above Compound | 8.0 | 970 | 121 |
| Compound of Synthesis Example 18 | 7.7 | >1000 | >125 |
| Racemic Mixture of the Above Compound | 8.0 | 628 | 79 |
| Compound of Synthesis Example 22 | 1.5 | >1000 | >667 |
| Racemic Mixture of the Above Compound | 3.6 | >1000 | >278 |

Industrial Applicability

The compounds of the present invention strongly and selectively inhibit [$^3$H]-5CT which binds to a human serotonin 5-HT$_7$ receptor subtype developed in a clonal cell system. Accordingly, the compound of the present invention and the pharmacologically acceptable salt thereof are useful for prevention or treatment of various diseases which are believed to be caused by the abnormality in the control function of serotonin present in the center and periphery. Examples of the disease include mental diseases (e.g., manic-depressive psychosis, anxiety, schizophrenia, epilepsy, sleep disorders, biological rhythm disorders, migraine and the like), cardiovascular diseases (e.g., hypertension and the like), and gastrointestinal diseases.

Further, from the intermediate of the present invention and the related production method provided by the present invention, a substance which more selectively binds to 5-HT₇ receptor is provided.

What is claimed is:

1. An optically active compound represented by the following formula (I):

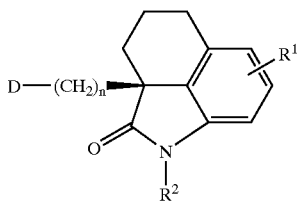

wherein D represents the following formula (IIIa), (IV) or (VI):

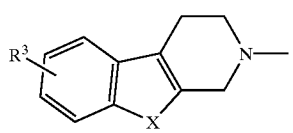

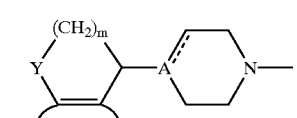

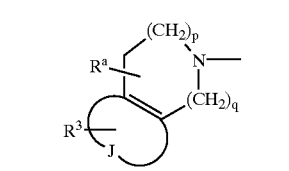

R¹ and R³ each independently represents (single or plural) a hydrogen atom, a halogen atom, a lower alkyl, a cyano, a trihalomethyl, a hydroxy, an alkoxy, an alkylthio, an alkylsulfinyl, an alkylsulfonyl, a carboxy, an alkoxycarbonyl, an acyl, an acyloxy, an acylthio, a sulfamoyl, a nitro, an amino, an alkylamino, a cabamoyl, an alkylcarbamoyl or a phenyl; R² represents a hydrogen atom, a lower alkyl or an aralkyl;

n represents an integer of 2 to 4;

A represents N, CH, C having a double bond or CR⁷, in which R⁷ represents a lower alkyl, a cyano, a carbamoyl, an alkylcarbamoyl, a carboxy, an acyl, an acyloxy, an alkoxy, an alkoxycarbonyl, a trihalomethyl or a hydroxy; ==== represents a single bond or a double bond;

E² represents a group forming a benzene ring, a pyridine ring or a pyrimidine ring together with a carbon atom having a double bond in a condensed part;

J represents a group forming a benzene ring, a thiophene ring, a furan ring, an imidazole ring or a pyrazole ring together with a carbon atom having a double bond in a condensed part; X represents NR⁸, NCONR⁹R¹⁰, S, SO, SO₂, or O, in which R⁸ represents a hydrogen atom, a lower alkyl, an aralkyl, an oxoalkyl, an alkenyl, a cyanoalkyl, a hydroxyalkyl, an alkoxyalkyl, an aminoalkyl, an alkylaminoalkyl, an alkoxycarbonylalkyl, a carbamoylalkyl, an alkylcarbamoylalkyl, an acyl or an alkoxycarbonyl, R⁹ and R¹⁰ each independently represents a hydrogen atom or a lower alkyl; Y represents CH₂, S, O or CO;

Rᵃ represents a hydrogen atom or an alkyl;

m represents an integer of 1 to 3;

p represents an integer of 0 or 1 to 3;

q represents an integer of 0 or 1 to 3, provided that p+q represents an integer of 1 to 3;

or the pharmacologically acceptable salt thereof.

2. An optically active compound as claimed in claim 1, wherein n is 4, or the pharmacologically acceptable salt thereof.

3. An optically active compound represented by the following formula (VIIIa):

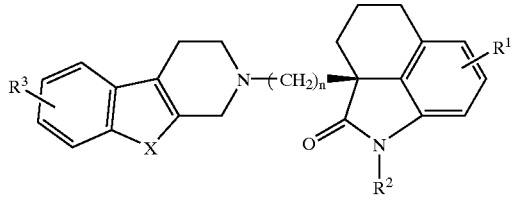

R¹ and R³ each independently represents (single or plural) a hydrogen atom, a halogen atom, a lower alkyl, a cyano, a trihalomethyl, a hydroxy, an alkoxy, an alkylthio, an alkylsulfinyl, an alkylsulfonyl, a carboxy, an alkoxycarbonyl, an acyl, an acyloxy, an acylthio, a sulfamoyl, a nitro, an amino, an alkylamino, a cabamoyl, an alkylcarbamoyl or a phenyl; R² represents a hydrogen atom, a lower alkyl or an aralkyl;

n represents an integer of 2 to 4;

X represents NR⁸, NCONR⁹R¹⁰, S, SO, SO₂, or O, in which R⁸ represents a hydrogen atom, a lower alkyl, an aralkyl, an oxoalkyl, an alkenyl, a cyanoalkyl, a hydroxyalkyl, an alkoxyalkyl, an aminoalkyl, an alkylaminoalkyl, an alkoxycarbonylalkyl, a carbamoylalkyl, an alkylcarbamoylalkyl, an acyl or an alkoxycarbonyl, R⁹ and R¹⁰ each independently represents a hydrogen atom or a lower alkyl; Y represents CH₂, S, O or CO;

wherein, or the pharmacologically acceptable salt thereof.

4. An optically active compound represented by the following formula (IX):

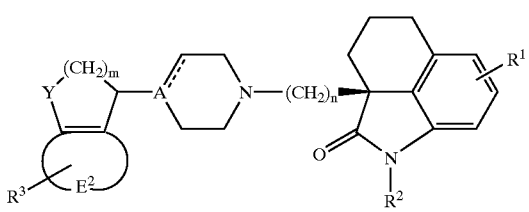

wherein R¹ and R³ each independently represents (single or plural) a hydrogen atom, a halogen atom, a lower alkyl, a cyano, a trihalomethyl, a hydroxy, an alkoxy, an alkylthio, an alkylsulfinyl, an alkylsulfonyl, a carboxy, an alkoxycarbonyl, an acyl, an acyloxy, an acylthio, a sulfamoyl, a nitro, an amino, an alkylamino, a cabamoyl, an alkylcarbamoyl or a phenyl; R₂ represents a hydrogen atom, a lower alkyl or an aralkyl;

n represents an integer of 2 to 4; A represents N, CH, C having a double bond or $CR^7$, in which $R^7$ represents a lower alkyl, a cyano, a carbamoyl, an alkylcarbamoyl, a carboxy, an acyl, an acyloxy, an alkoxy, an alkoxycarbonyl, a trihalomethyl or a hydroxy; === represents a single bond or a double bond; $E^2$ represents a group forming a benzene ring, a pyridine ring or a pyrimidine ring together with a carbon atom having a double bond in a condensed part; Y represents $CH_2$, S, O or CO; m represents an integer of 1 to 3, or the pharmacologically acceptable salt thereof.

5. An optically active compound as claimed in claim 4, wherein $E^2$ represents a group forming a pyridine ring or a pyrimidine ring together with a double bond; and A represents N, or the pharmacologically acceptable salt thereof.

6. An optically active compound represented by the following general formula (XI):

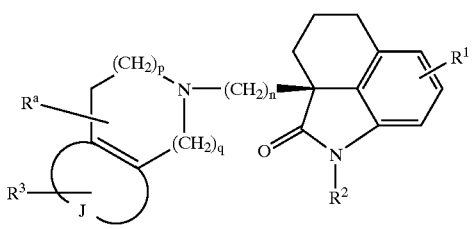

(XI)

wherein, $R^1$ and $R^3$ each independently represents (single or plural) a hydrogen atom, a halogen atom, a lower alkyl, a cyano, a trihalomethyl, a hydroxy, an alkoxy, an alkylthio, an alkylsulfinyl, an alkylsulfonyl, a carboxy, an alkoxycarbonyl, an acyl, an acyloxy, an acylthio, a sulfamoyl, a nitro, an amino, an alkylamino, a cabamoyl, an alkylcarbamoyl or a phenyl; $R^2$ represents a hydrogen atom, a lower alkyl or an aralkyl; J represents a group forming a benzene ring, a thiophene ring, a furan ring, an imidazole ring or a pyrazole ring together with a carbon atom having a double bond in a condensed part; $R^a$ represents a hydrogen atom or an alkyl; p represents an integer of 0 or 1 to 3;

q represents an integer of 0 or 1 to 3, provided that p+q represents an integer of 1 to 3;

n represents an integer of 2 to 4; or the pharmacologically acceptable salt thereof.

7. A pharmaceutical composition characterized by comprising an optically active compound described in anyone of claims 3, 4, 5 and 6 or the pharmacologically acceptable salt thereof and a pharmaceutically acceptable carrier.

8. A pharmaceutical method for the treatment of manic-depressive psychosis, sleep disorders and biological rhythm disorders comprising administering an optically active compound described in anyone of claims 3, 4, 5, and 6 or the pharmacologically acceptable salt thereof.

9. A method selectively binding the $5-HT_7$ receptor of a human comprising administering an optically active compound described in anyone of claims 3, 4, 5 and 6 or the pharmacologically acceptable salt thereof.

* * * * *